(12) United States Patent
Krishnan et al.

(10) Patent No.: US 9,388,385 B2
(45) Date of Patent: *Jul. 12, 2016

(54) METHODS FOR TREATING OBESITY AND/OR METABOLIC SYNDROME

(75) Inventors: Ravi Krishnan, Royston Park (AU); Silviu Itescu, Melbourne (AU)

(73) Assignee: MESOBLAST, INC., New York, NY (US)

( * ) Notice: Subject to any disclaimer, the term of this patent is extended or adjusted under 35 U.S.C. 154(b) by 44 days.

This patent is subject to a terminal disclaimer.

(21) Appl. No.: 14/118,862

(22) PCT Filed: May 18, 2012

(86) PCT No.: PCT/AU2012/000549
§ 371 (c)(1),
(2), (4) Date: Jun. 6, 2014

(87) PCT Pub. No.: WO2012/155209
PCT Pub. Date: Nov. 22, 2012

(65) Prior Publication Data
US 2014/0294775 A1 Oct. 2, 2014

Related U.S. Application Data

(60) Provisional application No. 61/488,037, filed on May 19, 2011.

(51) Int. Cl.
*C12N 5/0775* (2010.01)
*A61K 35/28* (2015.01)

(52) U.S. Cl.
CPC .............. *C12N 5/0663* (2013.01); *A61K 35/28* (2013.01)

(58) Field of Classification Search
CPC .................................................... C12N 5/0663
See application file for complete search history.

(56) References Cited

FOREIGN PATENT DOCUMENTS

| WO | WO 2006/072016 A2 | 7/2006 |
| WO | WO 2007/047604 A2 | 4/2007 |
| WO | WO 2010/057260 A1 | 5/2010 |

OTHER PUBLICATIONS

Bensidhoum et al. Blood, 2004, 103:3313-3319.*
Gronthos et al. Stem Cells and Development, 2007, 16:953-963.*
Ezquer et al. J of Hepatology, 2011, 55:1112-1120.*
International Search Report, mailed Jun. 7, 2012 in connection with PCT International Application No. PCT/AU2012/000549, filed May 18, 2012.
Written Opinion of the International Searching Authority, mailed Jun. 7, 2012 in connection with PCT International Application No. PCT/AU2012/000549, filed May 18, 2012.
Office Action issued May 12, 2015 in connection with Chinese Patent Application No. 201280031426.2.
Office Action issued May 12, 2015 in connection with Chinese Patent Application No. 201280031426.2 (English translation).
Notification Concerning Transmittal of international Preliminary Report on Patentability, (Chapter I of the Patent Cooperation Treaty), including an International Preliminary Report on Patentability and Written Opinion of the International Searching Authority, mailed Nov. 28, 2013 by the International Bureau of WIPO in connection with PCT International Application No. PCT/AU2012/000549, filed May 18, 2012.

* cited by examiner

*Primary Examiner* — Bin Shen
(74) *Attorney, Agent, or Firm* — John P. White; Cooper & Dunham LLP

(57) ABSTRACT

The present disclosure provides methods of treating or preventing obesity or causing weight loss or treating or preventing metabolic syndrome comprising administering to a subject a population of cells enriched for STRO-1+ cells and/or progeny thereof and/or soluble factors derived therefrom.

18 Claims, 12 Drawing Sheets

METHODS FOR TREATING OBESITY AND/OR METABOLIC SYNDROME

RELATED APPLICATION DATA

The present application claims priority from U.S. Provisional Patent Application No. 61/488,037 entitled "Method for treating obesity and/or metabolic syndrome", filed 19 May 2011, the entire contents of which are hereby incorporated by reference.

FIELD

The present disclosure relates to methods for treating or preventing obesity and/or metabolic syndrome.

BACKGROUND

Metabolic Syndrome

Metabolic syndrome {syn. syndrome X) is a complex disorder with high socioeconomic cost that is considered a worldwide epidemic. About 32% of people in USA are considered to suffer from metabolic syndrome, with the risk increasing with age (e.g., 40% of people aged between 40 and 60 are considered to suffer from this syndrome). Metabolic syndrome is associated with an increased risk of many disorders, such as, coronary heart disease, atherosclerotic disease, hypertension, stroke and type 2 diabetes. Currently, metabolic syndrome is diagnosed based on the presence of three or more of the following criteria:

Elevated waist circumference: definition of elevated depends on race, country and sex;

Elevated triglycerides: ≥150 mg/dL blood (1.7 mmol/L blood) or drug treatment for elevated triglycerides;

Reduced High density lipoprotein (HDL) cholesterol: <40 mg/dL blood (1.0 mmol/L blood) in men, <50 mg/dL blood (1.3 mmol/L blood) in women or drug treatment for low high density lipoprotein cholesterol;

Elevated blood pressure: systolic ≥130 mm Hg and/or diastolic >85 mm Hg or drug treatment for hypertension (or drug treatment for high blood pressure); and Elevated fasting glucose: >100 mg/dL blood (or drug treatment for hyperglycemia)

Current non-pharmacological therapies for metabolic syndrome include exercise and diet. Pharmacological treatments are generally targeted at one of the symptoms of metabolic syndrome. For example, compounds improving triglyceride and HDL levels have been suggested as useful for treating metabolic syndrome. However, these medications suffer from various undesirable side-effects. For example:

clofibrate (a fibric acid derivative) increases morbidity and mortality rates. Moreover, tumorigenicity has been demonstrated in rodents. Clinical trials have shown that some fibrates also cause reversible increases in serum creatinine levels.

Niacin has multiple adverse effects, the worst of which is chemical hepatitis. Other side effects include flushing, itching, and rash.

Statins are associated with muscle pain and rhabdomyolysis (which can lead to kidney failure and death), muscle weakness, neuropathy and memory loss. Furthermore, statins have a relatively short half life and require regular dosing to provide a therapeutic benefit. For example, atorvastatin has an effective half life of about 20-30 hours and in considered a long-acting statin.

It will be apparent from the foregoing that there is a need in the art for therapeutic/prophylactic methods for metabolic syndrome. Exemplary, therapeutic/prophylactic methods will treat or prevent several symptoms of metabolic syndrome.

Obesity

The incidence of obesity has increased dramatically throughout the world, most notably over the last 3 decades. By the year 2000, a total of 38.8 million American adults or 30% of the population of that country were classified as obese (i.e., having a body mass index score of at least 30 kg/m$^2$ for Caucasians, 25 kg/m$^2$ for Japanese and 28 kg/m$^2$ for Chinese). Obesity is associated with or thought to cause a number of diseases or disorders, and estimates attribute approximately 280,000 deaths each year in the United States to obesity related disorders.

Obesity is a risk factor for developing many obesity-related complications, from non-fatal debilitating conditions, such as, for example, osteoarthritis and respiratory disorders, to life-threatening chronic disorders, such as, for example, hypertension, type 2 diabetes, atherosclerosis, cardiovascular disease, some forms of cancer and stroke.

As the number of subjects that are obese is increasing (in the US alone the incidence of obesity increased one third in the last decade), the need to develop new and effective strategies in controlling obesity and obesity-related complications is becoming increasingly important.

Despite the high prevalence of obesity and many advances in our understanding of how it develops, current therapeutic strategies have persistently failed to achieve long-term success. Moreover, of the subjects that do lose weight, approximately 90 to 95 percent of subsequently regain their lost weight.

There are currently few therapeutic drugs approved by the FDA for the long term treatment of obesity. One of these compounds, orlistat, is a pancreatic lipase inhibitor that acts by blocking fat absorption into the body. However, the use of this drug is also accompanied by the unpleasant side effects of the passage of undigested fat from the body.

Another drug commonly used for the treatment of obesity is sibutramine, an appetite suppressant. Sibutramine is a β-phenethylamine that selectively inhibits the reuptake of noradrenaline and serotonin in the brain. Unfortunately, the use of sibutramine is also associated with elevated blood pressure and increased heart rate. As a result of these side effects dosage of sibutramine is limited to a level that is below the most efficacious dose.

Compounds for the short term treatment of obesity include, appetite suppressants, such as amphetamine derivatives. However, these compounds are highly addictive. Furthermore, subjects respond differently to these weight-loss medications, with some losing more weight than others and some not losing any weight whatsoever.

It will be apparent to the skilled artisan based on the foregoing, that there is a need in the art for methods of treating or preventing obesity or reducing body weight.

SUMMARY

The present inventors have found that they are able to reduce weight and/or treat obesity and/or treat metabolic syndrome in a non-human primate model using STRO-1$^+$ cell preparations. For example, the inventors have found that by administering STRO-1$^+$ cell preparations, they reduced levels of triglycerides and very low density lipoprotein (VLDL), increased levels of HDL, improved glucose tolerance, reduced fasting insulin and glucose levels and reduced weight. Thus, the inventors were able to treat numerous symptoms required for diagnosis of metabolic syndrome. The inventors have also shown that a single administration of the cell preparations provides a therapeutic benefit for at least three months and that multiple administrations can extend this time and increase the level of benefit.

The present disclosure provides a method of reducing weight of a subject, the method comprising administering to the subject a population of cells enriched for STRO-1$^+$ cells and/or progeny thereof and/or soluble factors derived therefrom.

In one example, the subject is overweight. In one example, the subject is obese.

In one example the subject suffers from type 2 diabetes. In another example, the subject does not suffer from type 2 diabetes.

The present disclosure additionally provides a method of treating or preventing obesity in a subject, the method comprising administering to the subject a population of cells enriched for STRO-1$^+$ cells and/or progeny thereof and/or soluble factors derived therefrom.

In one example, the administration of the population and/or the progeny and/or the soluble factors reduces body weight by at least about 3% or 3.5% about 4 weeks after the administration.

In one example, administration of the population and/or the progeny and/or the soluble factors reduces body weight by at least about 4% or 4.5% about 8 weeks after the administration.

In one example, administration of the population and/or progeny and/or the soluble factors reduces body weight by at least about 4% or 4.5% about 12 weeks after the administration.

For example, the reduction in body weight is after the initial administration of the cells.

In one example, the method comprises administering the population and/or progeny and/or the soluble factors at least twice. For example, each administration is separated by a period of about 12 weeks. In one example, the administration reduces body weight by at least about 5% by 16 weeks after the initial administration.

In one example, the method comprises administering the population and/or progeny and/or the soluble factors at least twice, wherein each administration is separated by a period of about 12 weeks and the administration reduces body weight by at least about 6% by 20 weeks after the initial administration.

In one example, administering the population and/or progeny and/or the soluble factors does not cause the subject to consume significantly less food and/or does not significantly reduce the subject's desire to consume food. This is not to say that the method does not additionally comprise consuming less food (e.g., compared to the amount consumed prior to treatment or earlier in the subject's treatment), only that the administration does not itself affect the subject's food consumption.

The present disclosure also provides a method of treating or preventing metabolic syndrome or a symptom thereof in a subject, the method comprising administering to the subject a population of cells enriched for STRO-1$^+$ cells and/or progeny thereof and/or soluble factors derived therefrom.

In one example, the symptom of metabolic syndrome is selected from the group consisting of elevated triglycerides, elevated low density lipoproteins, reduced high density lipoproteins, reduced lipoprotein index, elevated fasting glucose levels, elevated fasting insulin levels, reduced glucose clearance following feeding, insulin resistance, impaired glucose tolerance, obesity and combinations thereof.

In one example, the method reduces or prevents two or three or four or five or all of the foregoing symptoms.

In one example, administration of the population and/or the progeny and/or the soluble factors results in one or more of the following:
(i) reduced triglycerides;
(ii) reduced low density lipoproteins;
(iii) increased high density lipoproteins;
(iv) increased lipoprotein index;
(v) reduced fasting glucose levels;
(vi) reduced fasting insulin levels;
(vii) increased glucose clearance following feeding;
(viii) reduced insulin resistance; and
(ix) reduced body weight.

In one example, administration of the population and/or the progeny and/or the soluble factors results in two or three or four or five or all of the foregoing.

In one example, the method prevents progression or worsening of the metabolic syndrome and/or symptom thereof.

In one example, a method as described herein in any example comprises administering a population of cells enriched for STRO-1$^{bright}$ cells and/or progeny thereof and/or soluble factors derived therefrom.

In one example, a method as described herein in any example comprises administering a population of cells enriched for STRO-1$^+$ and tissue non-specific alkaline phosphatise$^+$ (TNAP)$^+$ cells and/or progeny thereof and/or soluble factors derived therefrom.

In one example, the population enriched for STRO-1$^+$ cells and/or progeny thereof and/or soluble factors derived therefrom are administered systemically. For example, the population and/or progeny and/or soluble factors are administered intravenously.

In one example, the population and/or the progeny and/or the soluble factors are administered a plurality of times.

For example, the population and/or the progeny and/or the soluble factors are administered once every two or more weeks.

For example, the population and/or the progeny and/or the soluble factors are administered once every three or more weeks.

For example, the population and/or the progeny and/or the soluble factors are administered once every four or more weeks.

In one example, the method comprises monitoring the subject and administering a further dose of the population and/or the progeny and/or the soluble factors when one or more of the following occurs:
(i) triglyceride levels increase to a level above that detected one month or two months after administration of the population and/or the progeny and/or the soluble factors or to a level similar to that detected before an initial administration of the population and/or the progeny and/or the soluble factors;
(ii) low density lipoprotein levels increase to a level above that detected one month or two months after administration of the population and/or the progeny and/or the soluble factors or to a level similar to that detected before an initial administration of the population and/or the progeny and/or the soluble factors;
(iii) high density lipoprotein levels decrease to a level above that detected one month or two months after administration of the population and/or the progeny and/or the soluble factors or to a level similar to that detected before an initial administration of the population and/or the progeny and/or the soluble factors;
(iv) lipoprotein index reduces to a level above that detected one month or two months after administration of the population and/or the progeny and/or the soluble factors or to a level similar to that detected before an initial administration of the population and/or the progeny and/or the soluble factors;
(v) fasting glucose levels increase to a level above that detected one month or two months after administration of the population and/or the progeny and/or the soluble factors or to a level similar to that detected before an initial administration of the population and/or the progeny and/or the soluble factors;
(vi) fasting insulin levels reduce to a level above that detected one month or two months after administration of the population and/or the progeny and/or the soluble factors or to a level similar to that detected before an initial administration of the population and/or the progeny and/or the soluble factors;
(vii) glucose clearance following feeding reduces to a level above that detected one month or two months after administration of the population and/or the progeny and/or the soluble factors or to a level similar to that detected before an initial administration of the population and/or the progeny and/or the soluble factors;
(viii) insulin resistance increases to a level above that detected one month or two months after administration of the population and/or the progeny and/or the soluble factors or to a level similar to that detected before an initial administration of the population and/or the progeny and/or the soluble factors; and
(ix) body weight increase to a level above that detected one month or two months after administration of the population and/or the progeny and/or the soluble factors or to a level similar to that detected before an initial administration of the population and/or the progeny and/or the soluble factors.

In one example, a method described herein according to any example comprises administering a dose of the population and/or the progeny and/or the soluble factors sufficient to achieve one or more of the following:
(i) reduce triglycerides;
(ii) reduce low density lipoproteins;
(iii) increase high density lipoproteins;
(iv) increase lipoprotein index;
(v) reduce fasting glucose levels;
(vi) reduce fasting insulin levels;
(vii) increase glucose clearance following feeding;
(viii) reduce insulin resistance; and
(ix) reduce body weight.

In one example, the dose is sufficient to achieve at least two or three or four of five or all of the foregoing.

In one example, a method described herein according to any example comprises administering between $0.1 \times 10^6$ to $5 \times 10^6$ STRO-1$^+$ cells and/or progeny thereof per kg.

In one example, a method described herein according to any example comprises administering between $0.3 \times 10^6$ to $2 \times 10^6$ STRO-1$^+$ cells and/or progeny thereof per kg. For example, the method comprises administering about $1 \times 10^6$ or $2 \times 10^6$ STRO-1$^+$ cells and/or progeny thereof per kg.

In one example, a method described herein according to any example comprises administering a low dose of STRO-1$^+$ cells and/or progeny thereof. For example, low dose of STRO-1$^+$ cells and/or progeny thereof comprises between $0.1 \times 10^5$ and $0.5 \times 10^6$ STRO-1$^+$ cells and/or progeny thereof per kg. For example, the low dose of STRO-1$^+$ cells and/or progeny thereof comprises about $0.3 \times 10^6$ STRO-1$^+$ cells and/or progeny thereof per kg.

In one example, the population and/or the progeny cells are autogeneic or allogeneic and/or the soluble factors can be derived from autogeneic or allogeneic cells. In one example, the population and/or the progeny are allogeneic and/or the soluble factors are from allogeneic cells.

In accordance with the above example, the method can additionally comprise obtaining the population and/or progeny cells and/or soluble factors or can additionally comprise isolating the population and/or progeny cells and/or soluble factors. In one example, the population and/or progeny cells are based on expression of STRO-1 and/or TNAP.

In one example, the population and/or progeny cells and/or soluble factors are obtained from the subject being treated. In another example, the population and/or progeny cells and/or soluble factors are obtained from a different subject of the same species.

In one example, the population enriched for STRO-1$^+$ cells and/or progeny cells have been culture expanded prior to administration and/or prior to obtaining the soluble factors.

In accordance with the above example, a method as described herein according to any example can additionally comprise culturing the population and/or progeny cells.

In one example, the STRO-1$^+$ cells and/or progeny cells thereof and/or soluble factors derived therefrom are administered in the form of a composition comprising said STRO-1$^+$ cells and/or progeny cells thereof and/or soluble factors derived therefrom and a carrier and/or excipient.

In accordance with the above example, a method as described herein according to any example can additionally comprise formulating the population and/or progeny and/or soluble factors into a composition.

In one example, the subject suffers from obesity and/or suffers from metabolic syndrome. For example, the subject is in need of treatment.

In one example, the subject is at risk of suffering from obesity and/or suffering from metabolic syndrome.

The present disclosure also provides a population of cells enriched for STRO-1$^+$ cells and/or progeny thereof and/or soluble factors derived therefrom for use in the treatment or prevention of obesity and/or metabolic syndrome and/or a symptom of metabolic syndrome.

The present disclosure also provides for use of a population of cells enriched for STRO-1$^+$ cells and/or progeny thereof and/or soluble factors derived therefrom in the manufacture of a medicament for treating or preventing obesity and/or metabolic syndrome and/or a symptom of metabolic syndrome in a subject.

The present disclosure also provides a kit comprising a population of cells enriched for STRO-1$^+$ cells and/or progeny thereof and/or soluble factors derived therefrom packaged with instructions for use in a method described herein according to any example.

For example, the present disclosure provides a kit comprising a composition comprising the population and/or the progeny and/or the soluble factors packaged with product information indicating use of the composition in a method described herein according to any example.

(IgG) and 1A6.12 (IgM) treated under the same conditions. The results demonstrate that a minor population of STRO-1$^{bright}$ cells co-expressed TNAP (upper right quadrant) while the remaining STRO-1$^+$ cells failed to react with the STRO-3 mAb.

Figure 2:
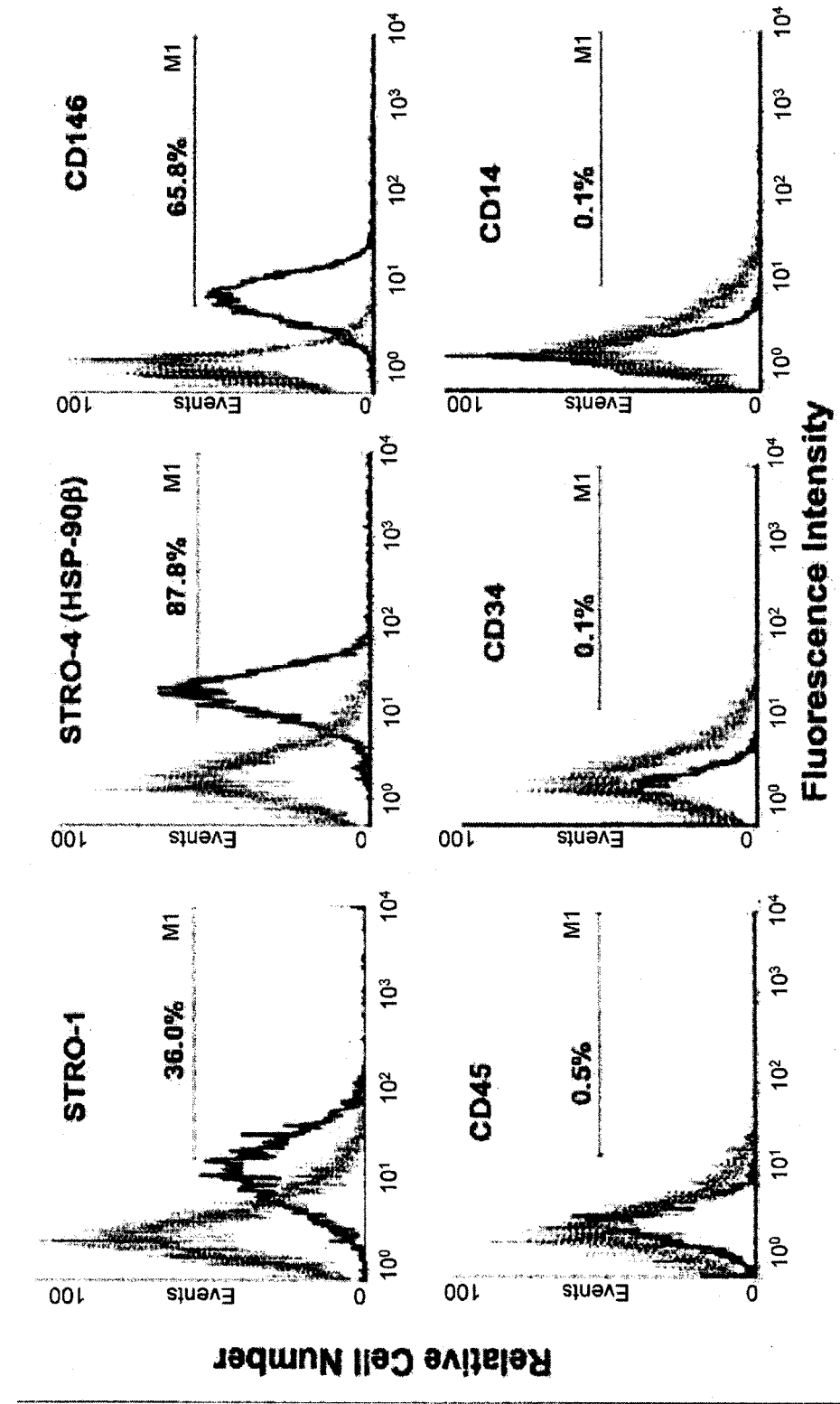

FIG. 2. Graphical representations showing representative flow cytometric histograms produced using single cell suspensions of culture expanded bone marrow derived cynomolgus MPCs with positive cell surface expression of the mesenchymal stem cell markers, STRO-1, STRO-4 and CD 146 (solid) relative to the isotype (IgM, IgG2a and IgG1) negative controls (hashed) detected using goat anti-murine IgM or IgG conjugated-FITC secondary antibodies. Representative histograms also show that cynomolgus MPCs lack cell surface expression for markers of monocyte/macrophage (CD 14), haematopietic stem/progenitor cells (CD34) and mature leukocyte (CD45). Levels of greater than 1% fluorescence compared to the isotype control signify positivity.

Figure 3:
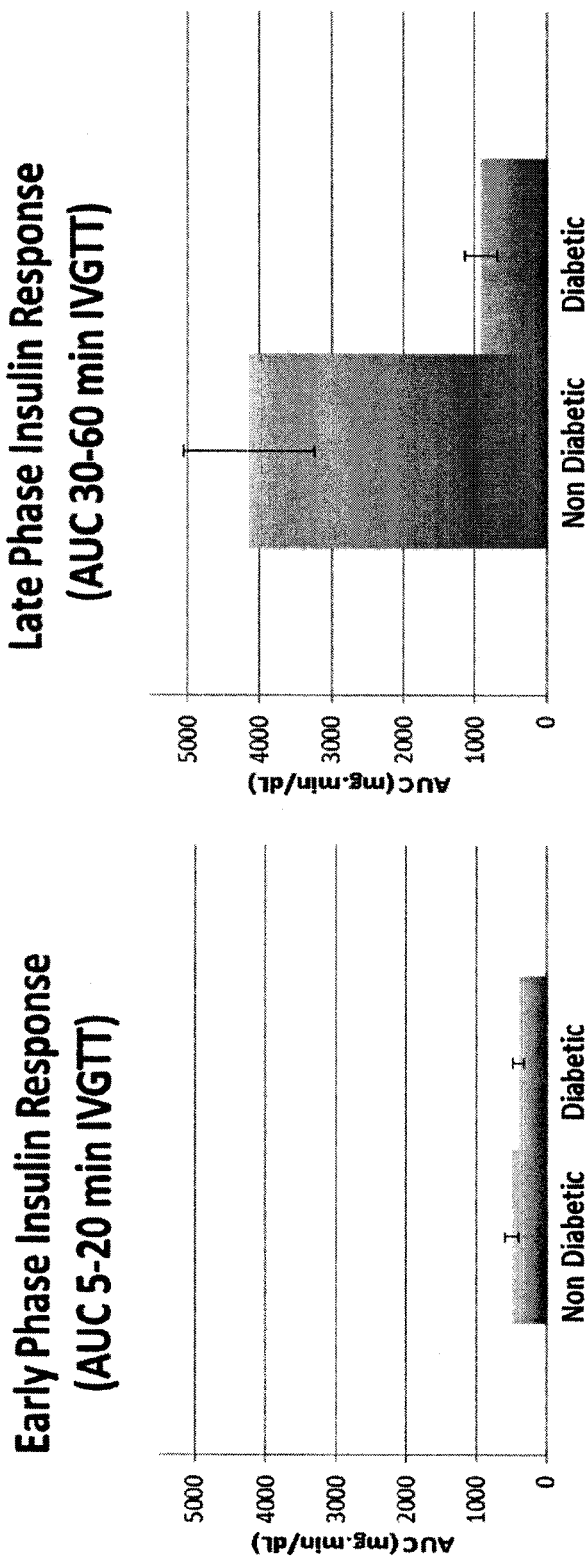

FIG. 3. Graphical representation showing mean area under the curve (AUC), over a one month period of repeated evaluation, for insulin response at early phase (5-20 minutes; left hand side) and late phase (30-60 minutes; right hand side) following intravenous glucose tolerance test (IVGTT). Tests were performed in diabetic and non-diabetic animals (as indicated).

Figure 4:
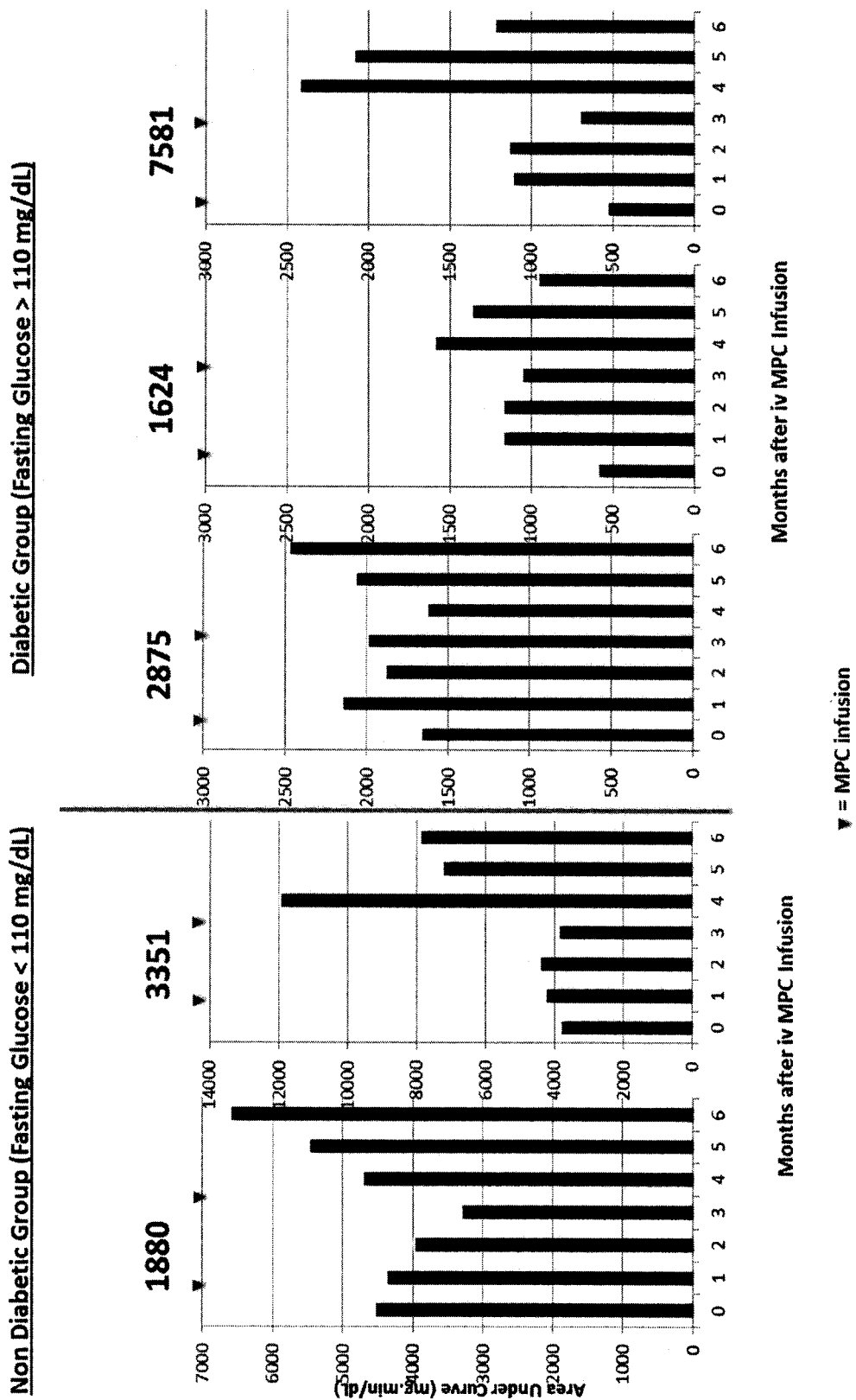

FIG. 4. Graphical representation showing the mean monthly Area Under the Curve (AUC3o-60 min) late phase insulin response following intravenous infusion of glucose. Individual data for each non-diabetic and diabetic animal (as indicated) for a month before and 6 months after MPC treatment are depicted. Arrows indicate the time at which MPC were infused.

Figure 5:
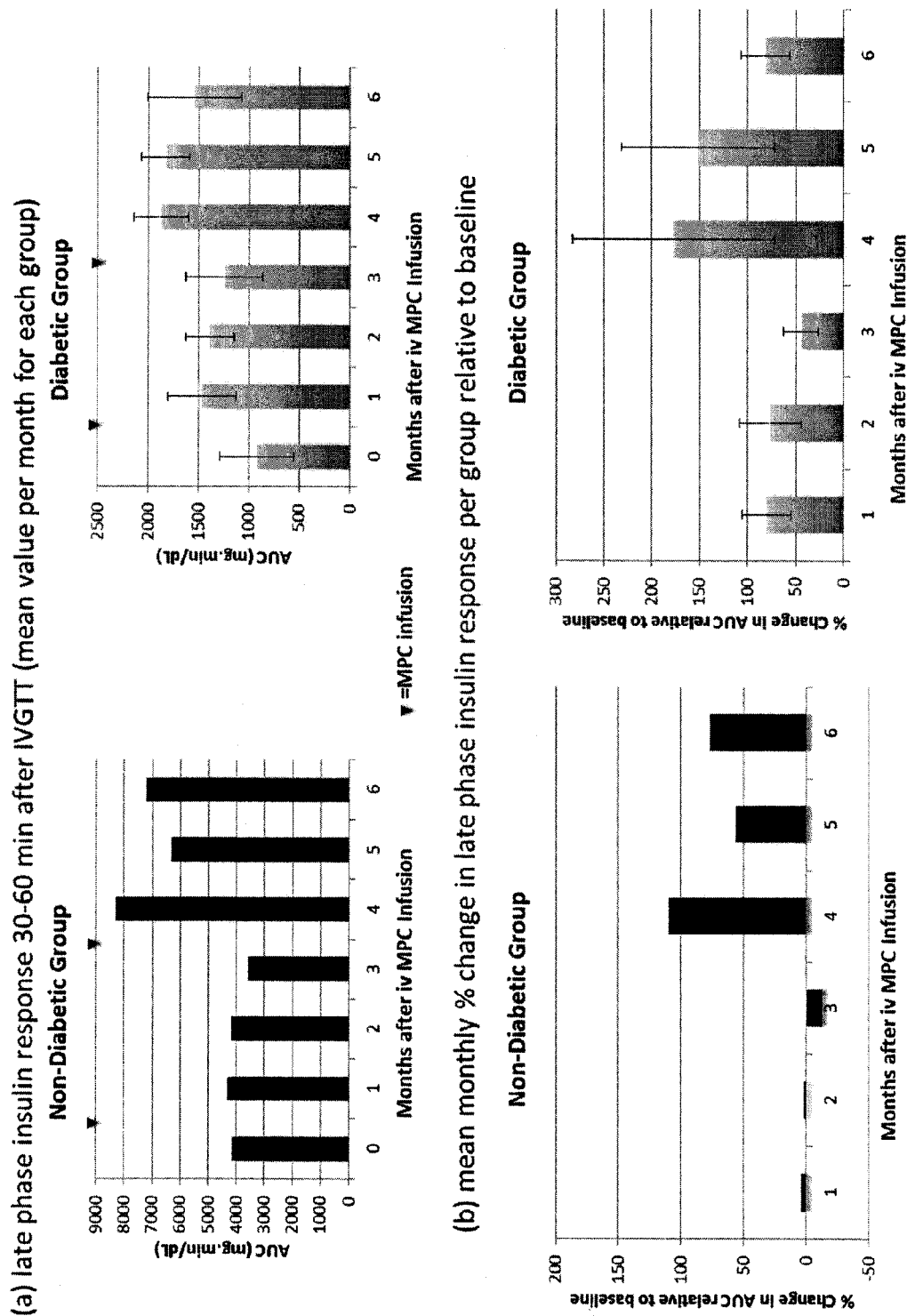

FIG. 5. Graphical representations showing that successive doses of MPCs induce a progressive increase in late-phase insulin response to glucose loading. The representations in Panel (a) show the mean monthly Area Under the Curve (AUC$_{30-60min}$) late phase insulin response following intravenous infusion of glucose for the groups of non-diabetic and diabetic animals (as indicated). Data for non-diabetic and diabetic groups for a month before and 6 months after MPC treatment are depicted. Arrows indicate the time at which MPC were infused. Representations in Panel 3(b) illustrate the mean monthly percentage change in late phase insulin response per group relative to the untreated baseline values.

Figure 6:
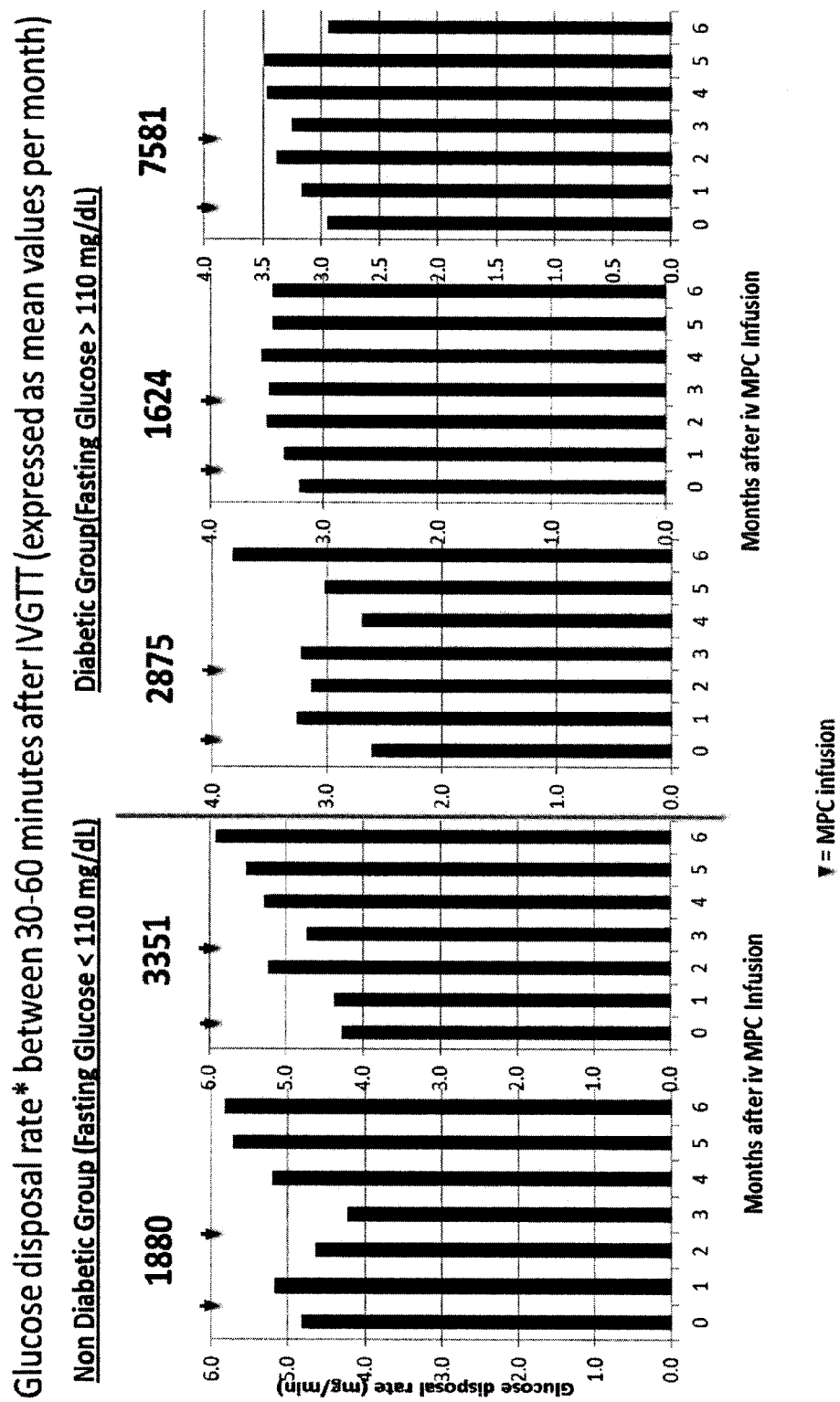

FIG. 6. Graphical representation showing the mean monthly blood glucose clearance rate during the late phase insulin response (30-60 min) following intravenous infusion of glucose. Individual data for each non-diabetic and diabetic animal (as indicated) for a month before and 6 months after MPC treatment are demonstrated. Arrows indicate the time at which MPCs were infused.

Figure 7:
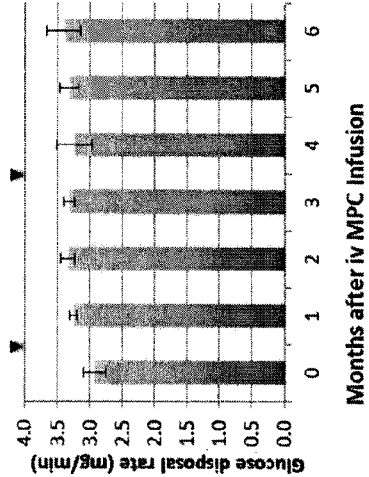
Figure 7:
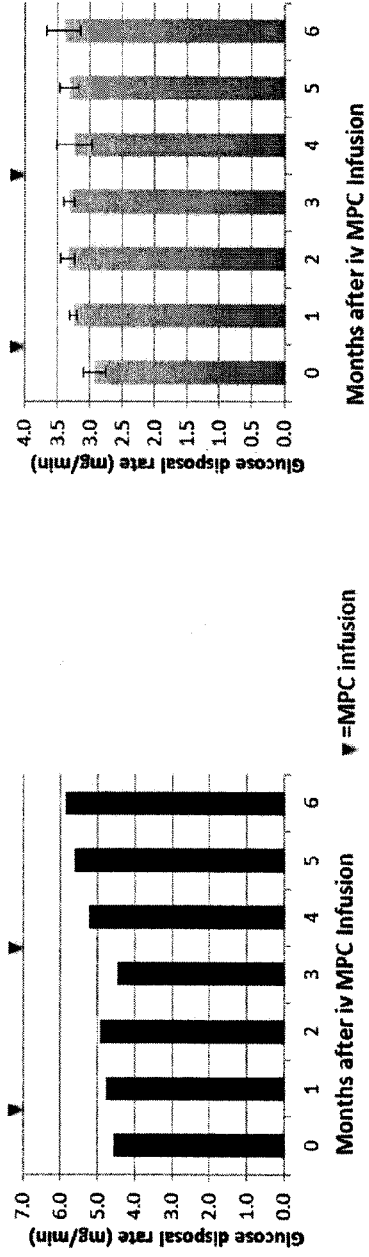
Figure 7:
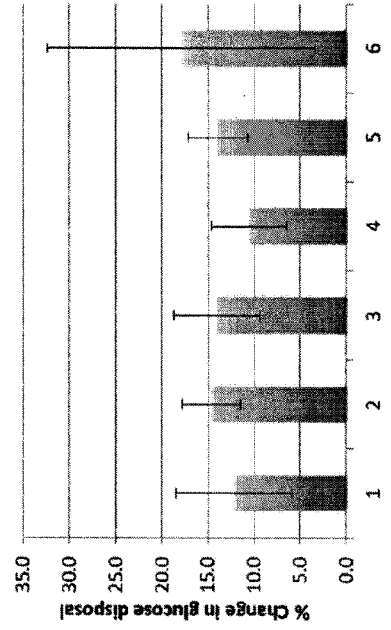
Figure 7:
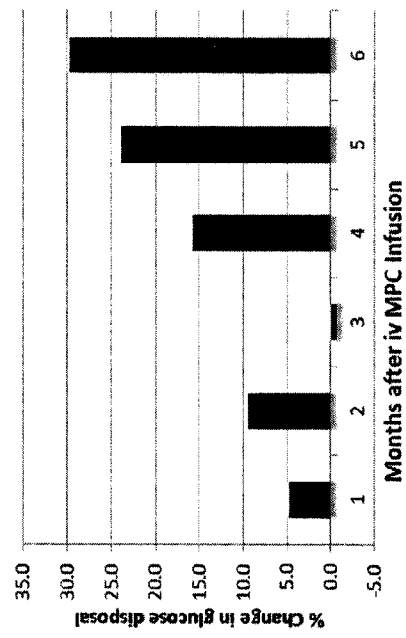

FIG. 7. Graphical representations showing MPCs induce a progressive increase in glucose clearance after high glucose load. Panel (a) shows the mean monthly blood glucose clearance rate during the late phase insulin response (30-60 min) following intravenous infusion of glucose. Individual data for the non-diabetic and diabetic groups for a month before and 6 months after MPC treatment are depicted. Arrows indicate the time at which MPCs were infused. Panel 5(b) depicts the mean monthly percentage change in glucose disposal rate per group relative to pretreatment baseline.

Figure 8:
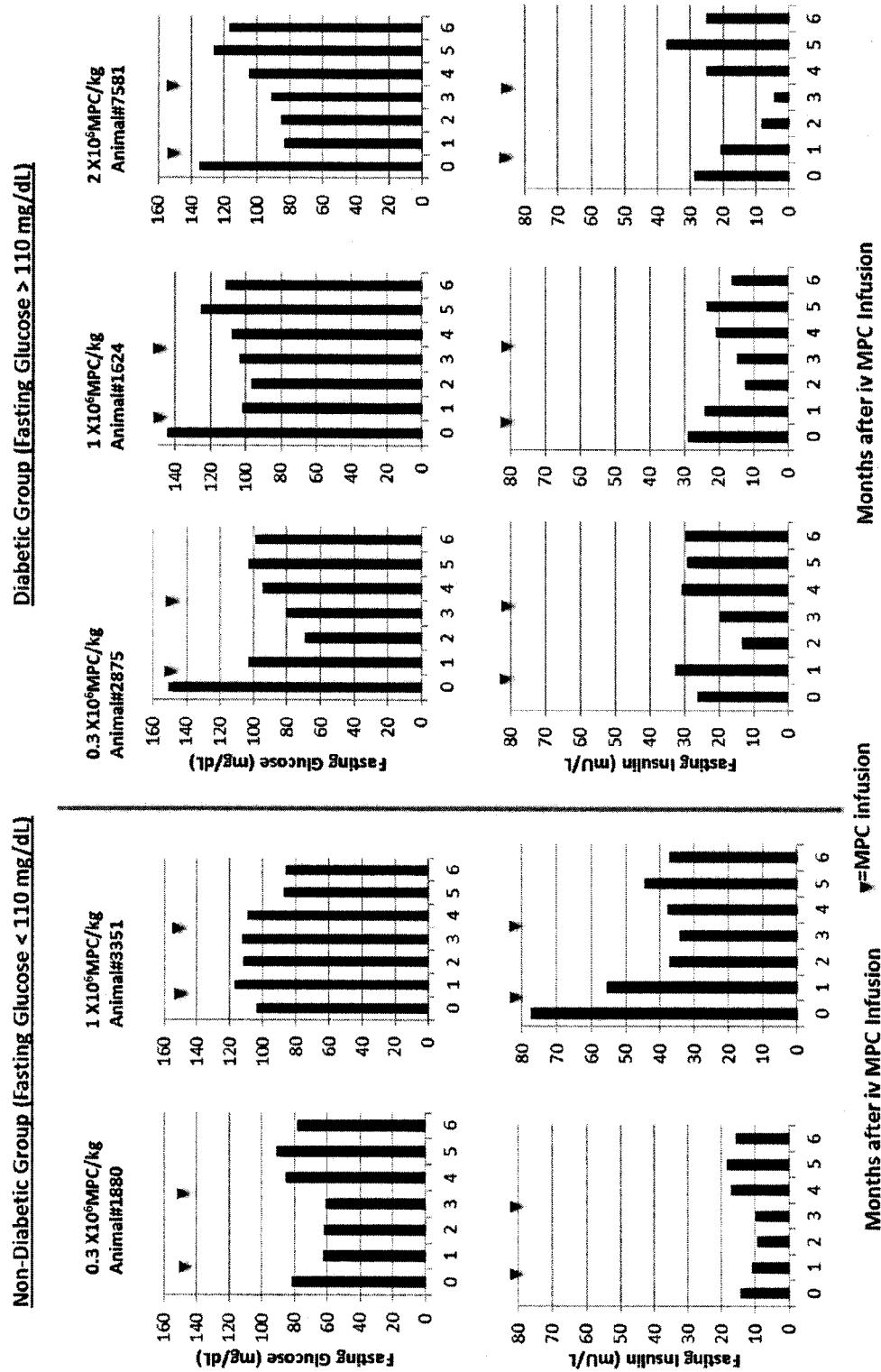

FIG. 8. Graphical representations showing the mean monthly fasting blood glucose levels (top panels) and the mean monthly fasting insulin levels (bottom panels) in monkeys treated with MPCs. Individual data for the non-diabetic (fasting BGL at baseline>110 mg/dL) and diabetic (fasting BGL<110 mg/dL at baseline) animals for a month before and 6 months after MPC treatment are depicted. Arrows indicate the time at which MPCs were infused. MPC dosage for each animal is indicated.

Figure 9:
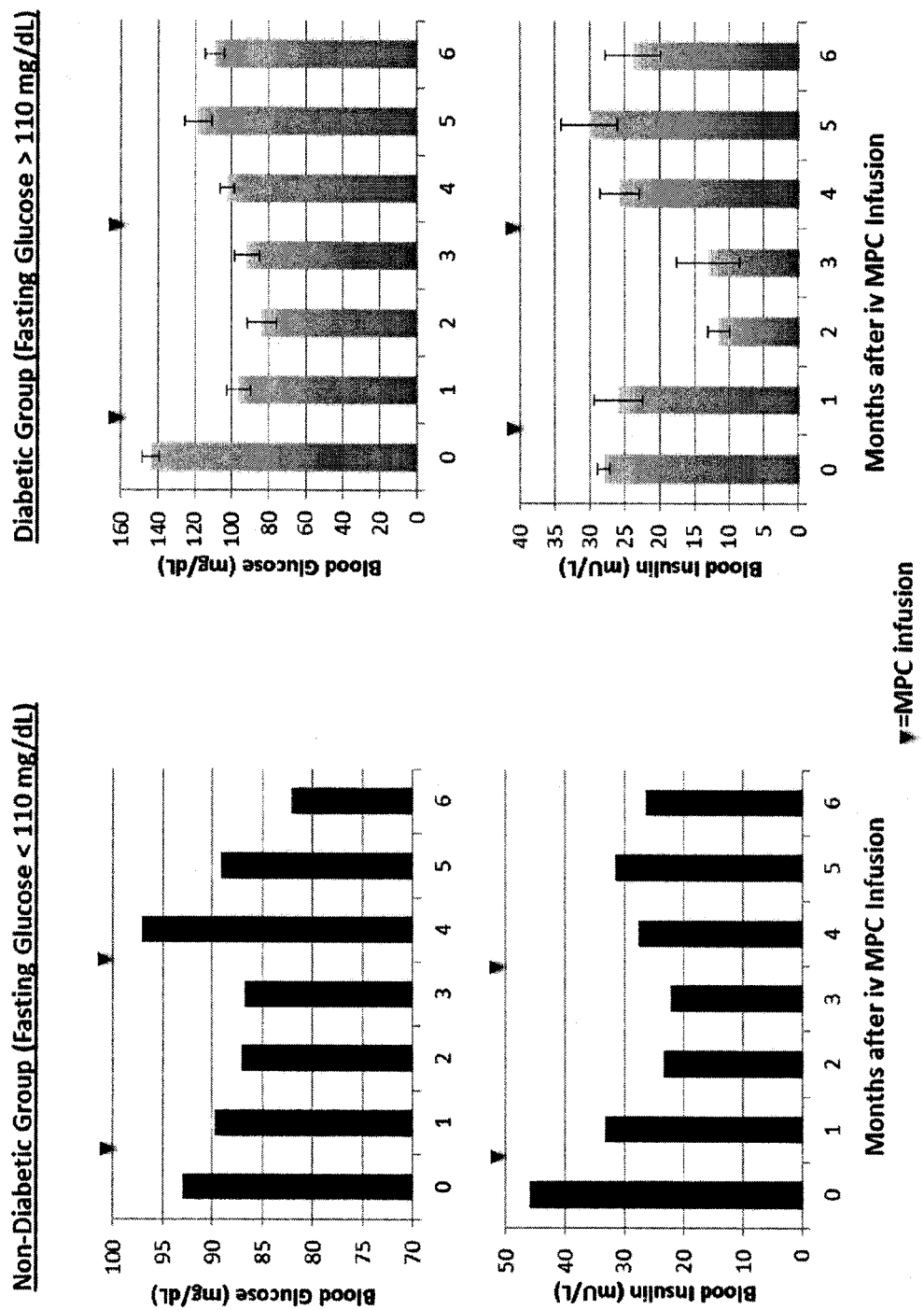

FIG. 9. Graphical representations showing the mean monthly fasting blood glucose levels (top panels) and the mean monthly fasting insulin levels (bottom panels) of animals administered MPCs. Data for the non-diabetic (fasting BGL at baseline>110 mg/dL) and diabetic (fasting BGL<110 mg/dL at baseline) animal groups for a month before and 6 months after MPC treatment are depicted. Arrows indicate the time at which MPCs were infused.

Figure 10:
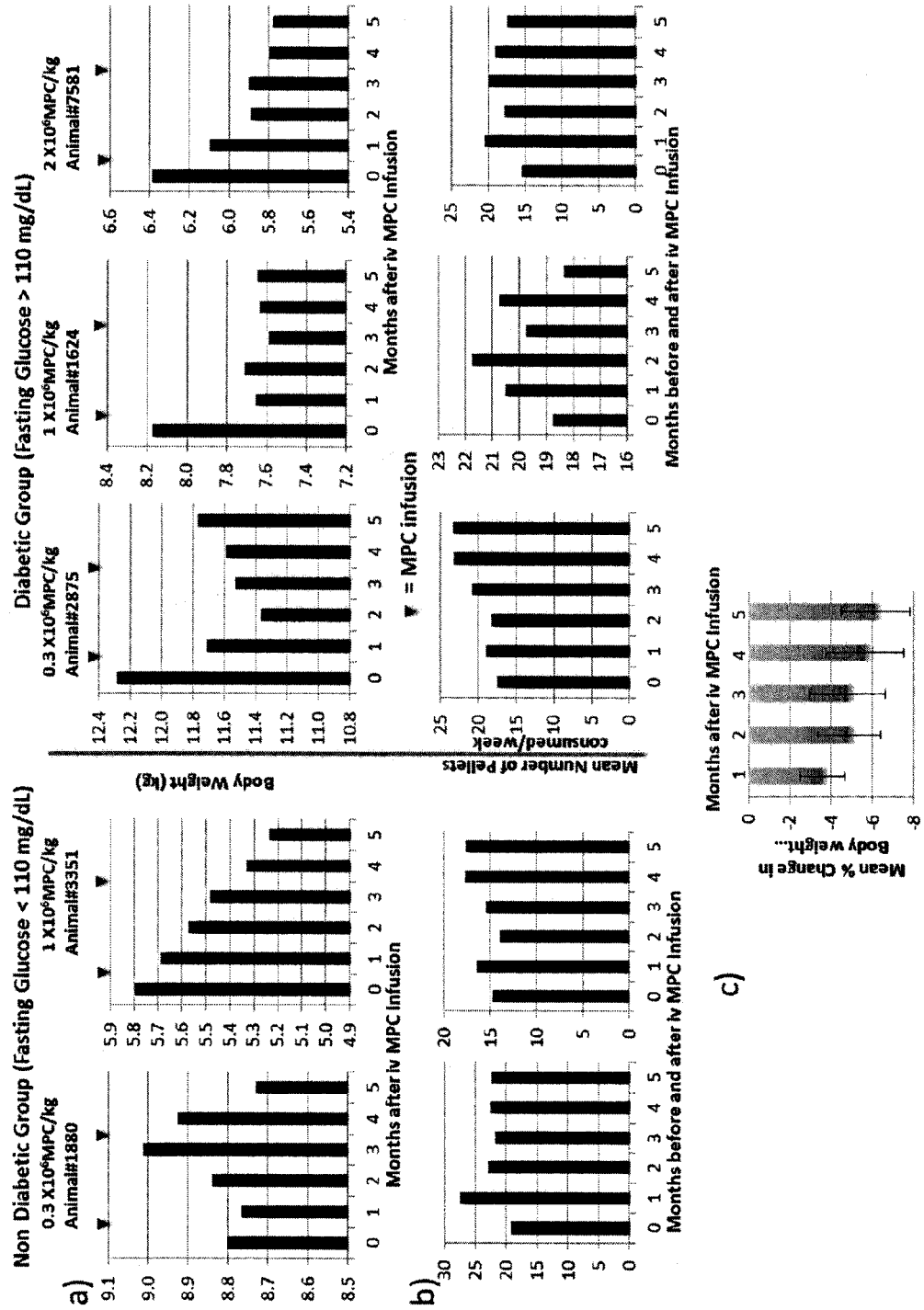

FIG. 10. Graphical representations showing MPC treatment induces sustained weight loss, despite continued high dietary intake. Panel (a) shows the mean monthly body weight changes in both non-diabetic and diabetic animals. Individual data for the non-diabetic and diabetic animals for a month before and 6 months after MPC treatment are depicted. Arrows indicate the time at which MPCs were infused. Dosage of MPC for each animal is shown on the top of each panel. Panel (b) shows the amount of food consumed (mean number of pellets consumed per week) for each individual animal throughout the period of weight measurements. Panel (c) shows the mean monthly percentage weight loss in the pooled group of animals after MPC therapy relative to the untreated baseline. The weight loss ranged from 4% to 6% during the course of MPC treatment.

Figure 11:
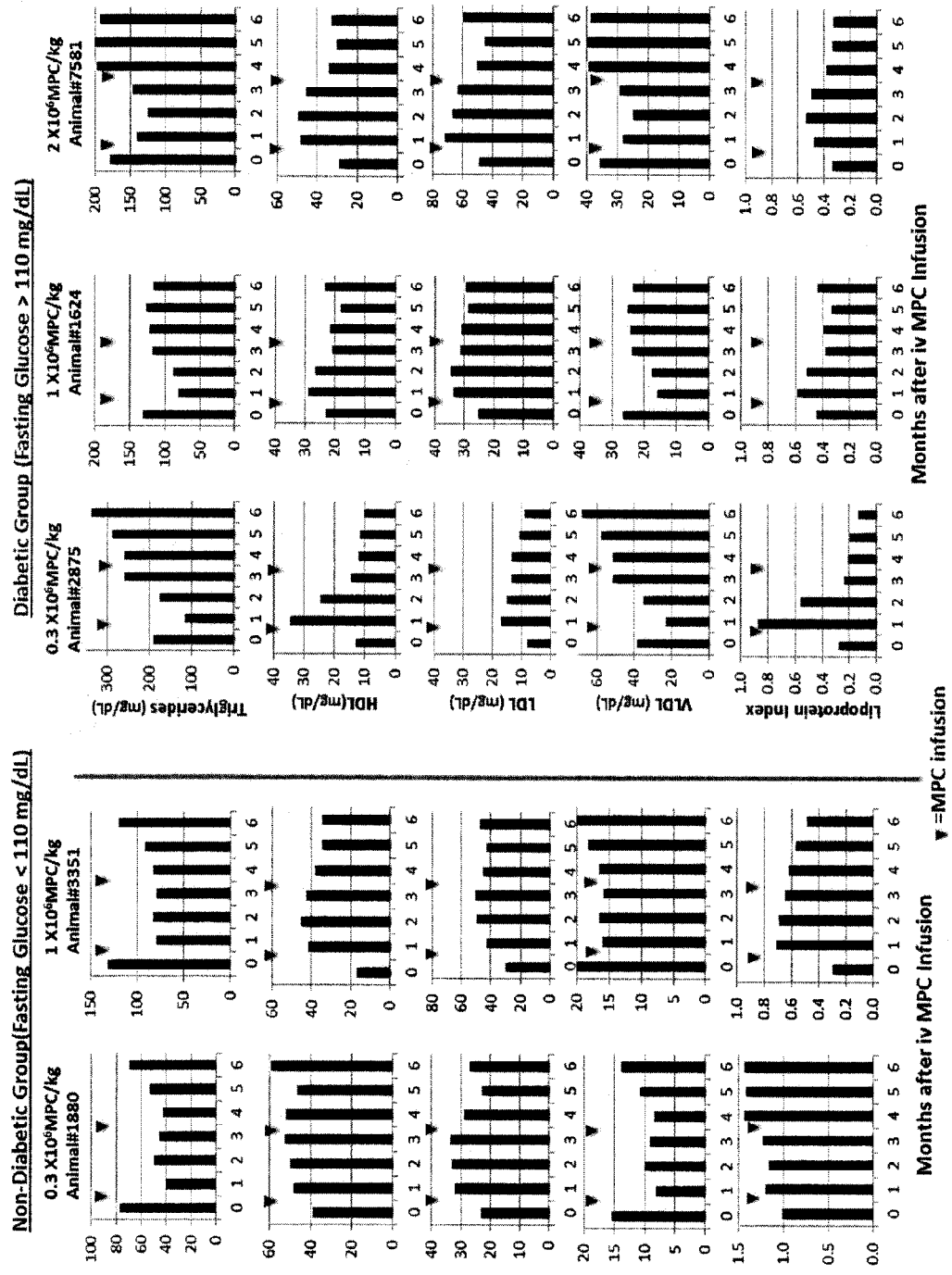

FIG. 11. Graphical representations showing monthly fasting lipid profiles (as indicated) in non-diabetic and diabetic animals. Individual data for non-diabetic and diabetic animals for a month before and 6 months after MPC treatment are depicted. Arrows indicate the time at which MPCs were infused. Dosage of MPC for each animal is shown on the top of each panel.

Figure 12:
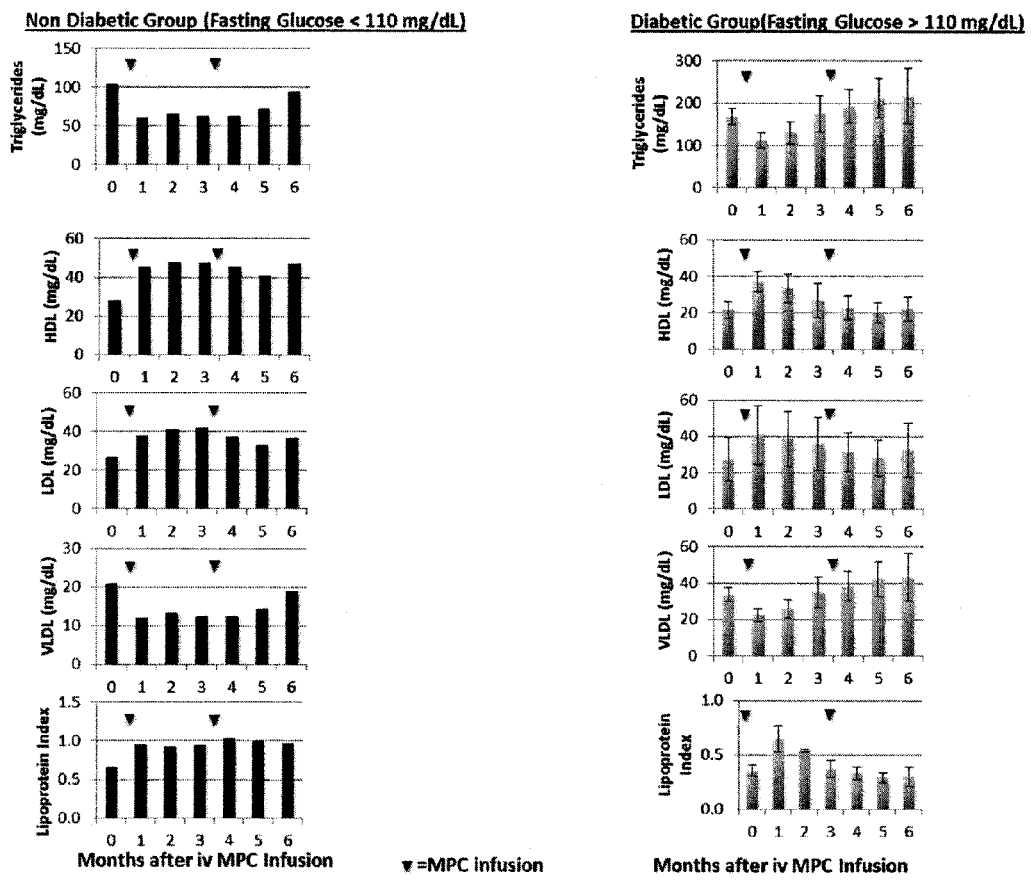

FIG. 12. Graphical representations showing mean monthly fasting lipid profiles (as indicated) in non-diabetic and diabetic animals. Data for the non-diabetic and diabetic groups for a month before and 6 months after MPC treatment are depicted. Arrows indicate the time at which MPCs were infused.

DETAILED DESCRIPTION

General Techniques and Selected Definitions

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each example described herein is to be applied mutatis mutandis to each and every other example of the disclosure unless specifically stated otherwise.

Those skilled in the art will appreciate that the present disclosure and individual examples thereof are susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples of the disclosure included herein, which are intended for the purpose of exemplification only. Functionally-equivalent products, compositions and methods are clearly within the scope of the disclosure and examples thereof, as described herein.

The present disclosure is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in Sambrook, Fritsch & Maniatis, Molecular Cloning: A Laboratory Manual, Cold Spring Harbor Laboratories, New York, Second Edition (1989), whole of Vols I, II, and III; DNA Cloning: A Practical Approach, Vols. I and II (D. N. Glover, ed., 1985), IRL Press, Oxford, whole of text; Oligonucleotide Synthesis: A Practical Approach (M. J. Gait, ed, 1984) IRL Press, Oxford, whole of text, and particularly the papers therein by Gait, pp 1-22; Atkinson et al, pp 35-81; Sproat et al, pp 83-115; and Wu et al, pp 135-151; 4. Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series; J. F. Ramalho Ortigao, "The Chemistry of Peptide Synthesis" In: Knowledge database of Access to Virtual Laboratory website (Interactiva, Germany); Sakakibara, D., Teichman, J., Lien, E. Land Fenichel, R. L. (1976). *Biochem. Biophys. Res. Commun.* 73 336-342; Merrifield, R. B. (1963). *J. Am. Chem. Soc.* 85, 2149-2154; Barany, G. and Merrifield, R. B. (1979) in The Peptides (Gross, E. and Meienhofer, J. eds.), vol. 2, pp. 1-284, Academic Press, New York. 12. Wunsch, E., ed. (1974) Synthese von Peptiden in Houben-Weyls Metoden der Organischen Chemie (Muler, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky, M. (1985) *Int. J. Peptide Protein Res.* 25, 449-474; Handbook of Experimental Immunology, Vols. I-IV (D. M. Weir and C. C. Blackwell, eds., 1986, Blackwell Scientific Publications); and Animal Cell Culture Practical Approach, Third Edition (John R. W. Masters, ed., 2000), ISBN 0199637970, whole of text.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

As used herein the term "derived from" shall be taken to indicate that a specified integer may be obtained from a particular source albeit not necessarily directly from that source. In the context of soluble factors derived from STRO-1$^+$ cells and/or progeny cells thereof, this term shall be taken to mean one or more factors, e.g., proteins, peptides, carbohydrates, etc, produced during in vitro culturing of STRO-1$^+$ cells and/or progeny cells thereof.

As used herein, the term "elevated triglycerides" will be understood to mean about 150 mg triglycerides or more per dL blood (1.7 mmol/L blood). Methods for assessing lipid and/or lipoprotein levels in a subject will be apparent to the skilled artisan and include, ultracentrifugation, immunoassays.

As used herein, the term "elevated low density lipoprotein (LDL)" will be understood to mean 100 mg LDL or more per dL blood, or 70 mg LDL or more per dL for people suffering from heart disease or atherosclerosis. Methods for assessing lipid and/or lipoprotein levels in a subject will be apparent to the skilled artisan and include, ultracentrifugation, immunoassays.

As used herein, the term "reduced high density lipoprotein (HDL) cholesterol" will be understood to mean 40 mg HDL or less per dL blood (1.0 mmol/L blood) or less in men or 50 mg HDL or less per dL blood (1.3 mmol/L blood) in women. Methods for assessing lipid and/or lipoprotein levels in a subject will be apparent to the skilled artisan and include, ultracentrifugation, immunoassays.

As used herein, the term "lipoprotein index" will be understood to mean the ratio of HDL to non-HDL cholesterol. Thus, the higher the level of HDL and/or the lower the level of non-HDL cholesterol, the higher the ratio.

As used herein, the term "elevated fasting glucose levels" will be understood to mean a fasting plasma glucose level from 5.6 mmol glucose per L of plasma (or 100 mg glucose per dL of plasma) to 6.9 mmol glucose per L of plasma (or 125 mg glucose per dL of plasma).

As used herein, the term "elevated fasting insulin levels" will be understood to mean a fasting insulin level of greater than about 60 pmol/L. This is also evidence of insulin resistance.

As used herein, the term "impaired glucose tolerance" will be understood to mean a plasma glucose concentration of 7.8 mmol/dL (140 mg/dL) or greater (e.g., from 7.8 to 11 mmol/dL (140-197 mg/dL) two hours after ingesting a 75 gram oral dose of glucose. This definition also contemplates accepted definitions, e.g., assessed using an intravenous glucose tolerance test.

As used herein, the term "insulin resistance" encompasses a condition characterized by impaired glucose tolerance and/or elevated fasting insulin levels.

As used herein, the term "overweight" or "excessive weight" will be understood to mean a body mass index of 25 or more. In some examples, this term encompasses obesity. In some examples, this term encompasses pre-obesity, i.e., a BMI of 25-30. Other clinically accepted definitions of "overweight" are also contemplated by this term. Subjects that are overweight are also considered at risk of developing obesity.

Reference herein to a subject "at risk of developing metabolic syndrome" includes subjects in their sixth decade and/or subjects of Hispanic and/or Asian race and/or a greater than or equal to 25 and/or subject s with a family history of type 2 diabetes and/or a family history of diabetes during pregnancy (gestational diabetes) and/or a family history of obesity and/or a diagnosis of one or more of high blood pressure, cardiovascular disease or polycystic ovary syndrome.

As used herein, the term "effective amount" shall be taken to mean a sufficient quantity of STRO-1$^+$ cells and/or progeny cells thereof and/or soluble factors derived therefrom to achieve one or more of the following:
(i) reduce triglycerides;
(ii) reduce low density lipoproteins;
(iii) increase high density lipoproteins;
(iv) increase lipoprotein index;
(v) reduce fasting glucose levels;
(vi) increase insulin secretion by the pancreas;
(vii) increase glucose clearance following feeding;
(viii) reduce insulin resistance; and
(ix) reduce body weight.

As used herein, the term "therapeutically effective amount" shall be taken to mean a sufficient quantity of STRO-1$^+$ cells and/or progeny cells thereof and/or soluble factors derived therefrom to treat metabolic syndrome and/or obesity, i.e., such that the subject no longer satisfies the clinical criteria for metabolic syndrome and/or obesity. For example, the weight of an obese subject is reduced to a point where the subject is no longer obese (e.g., they may be overweight or normal).

As used herein, the term "prophylactically effective amount" shall be taken to mean a sufficient quantity of STRO-1+ cells and/or progeny cells thereof and/or soluble factors derived therefrom to prevent or inhibit or delay the onset of metabolic syndrome and/or obesity, e.g., preventing a subject from developing the clinical criteria for a diagnosis of metabolic syndrome and/or obesity. For example, an overweight subject is treated such that they do not continue to increase in weight to a point at which they are obese.

As used herein, the term "low dose" shall be understood to mean an amount of STRO-1+ cells and/or progeny thereof less than $1\times10^6$, yet still sufficient to be an "effective amount" as defined herein and/or a "therapeutically effective amount" and/or a "prophylactically effective amount" as defined herein. For example, a low dose comprises $0.5\times10^6$ or fewer cells, or $0.4\times10^6$ or fewer cells or $0.3\times10^6$ or fewer cells or $0.1\times10^6$ or fewer cells.

As used herein, the term "treat" or "treatment" or "treating" shall be understood to mean administering a therapeutically effective amount of soluble factors and/or cells and reducing or inhibiting symptom(s) of metabolic syndrome such that the subject is no longer clinically diagnosed with the syndrome and/or reducing the weight of a subject such that they are no longer obese.

As used herein, the term "prevent" or "preventing" or "prevention" shall be taken to mean administering a prophylactically effective amount of soluble factors and/or cells and stopping or hindering or delaying the development or progression of metabolic syndrome and/or to stop or hinder or delay development of obesity.

As used herein, the term "soluble factors" shall be taken to mean any molecule, e.g., protein, peptide, glycoprotein, glycopeptide, lipoprotein, lipopeptide, carbohydrate, etc. produced by STRO-1+ cells and/or progeny thereof that are water soluble. Such soluble factors may be intracellular and/or secreted by a cell. Such soluble factors may be a complex mixture (e.g., supernatant) and/or a fraction thereof and/or may be a purified factor. In one example, soluble factors are or are contained within supernatant. Accordingly, any example herein directed to administration of one or more soluble factors shall be taken to apply mutatis mutandis to the administration of supernatant.

As used herein, the term "supernatant" refers to the non-cellular material produced following the in vitro culturing of STRO-1+ cells and/or progeny thereof in a suitable medium, for example, liquid medium. Typically, the supernatant is produced by culturing the cells in the medium under suitable conditions and time, followed by removing the cellular material by a process such as centrifugation. The supernatant may or may not have been subjected to further purification steps before administration. In one example, the supernatant comprises less than $10^5$, more such as, less than $10^4$, for example, less than $10^3$, e.g., no live cells.

As used herein, the term "normal or healthy individual" shall be taken to mean a subject that does not suffer from metabolic syndrome or obesity as assessed by any method known in the art and/or described herein. In one example, a "normal or healthy individual" does not suffer from any of the symptoms of metabolic syndrome and/or has a BMI of less than 35.

STRO-1+ Cells or Progeny Cells, and Supernatant or One or More Soluble Factors Derived Therefrom STRO-r cells are cells found in bone marrow, blood, deciduous teeth (e.g., exfoliated deciduous teeth), dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis, and periosteum.

In one example, STRO-1+ cells are capable of differentiating into one or more or two or more and/or three germ lines such as mesoderm and/or endoderm and/or ectoderm.

In one example, the STRO-1+ cells are multipotential cells which are capable of differentiating into a large number of cell types including, but not limited to, adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues. STRO-1+ multipotential cells are thus non-hematopoietic progenitor cells which divide to yield daughter cells that are either stem cells or are precursor cells which in time will irreversibly differentiate to yield a phenotypic cell.

In one example, the STRO-1+ cells are enriched from a sample obtained from a subject, e.g., a subject to be treated or a related subject or an unrelated subject (whether of the same species or different). The terms "enriched", "enrichment" or variations thereof are used herein to describe a population of cells in which the proportion of one particular cell type or the proportion of a number of particular cell types is increased when compared with an untreated population of the cells (e.g., cells in their native environment). In one example, a population enriched for STRO-1+ cells comprises at least about 0.1% or 0.5% or 1% or 2% or 5% or 10% or 15% or 20% or 25% or 30% or 50% or 75% STRO-1+_cells. In this regard, the term "population of cells enriched for STRO-1+ cells" will be taken to provide explicit support for the term "population of cells comprising X % STR01+ cells", wherein X % is a percentage as recited herein. The STRO-1+ cells can, in some examples, form clonogenic colonies, e.g. CFU-F (fibroblasts) or a subset thereof (e.g., 50% or 60% or 70% or 70% or 90% or 95%) can have this activity.

In one example, the population of cells is enriched from a cell preparation comprising STRO-r cells in a selectable form. In this regard, the term "selectable form" will be understood to mean that the cells express a marker (e.g., a cell surface marker) permitting selection of the STRO-1+ cells. The marker can be STRO-1, but need not be. For example, as described and/or exemplified herein, cells (e.g., MPCs) expressing STRO-2 and/or STRO-3 (TNAP) and/or STRO-4 and/or VCAM-1 and/or CD146 and/or 3G5 also express STRO-1 (and can be STRO-1$^{bright}$). Accordingly, an indication that cells are STRO-1+ does not mean that the cells are selected by STRO-1 expression. In one example, the cells are selected based on at least STRO-3 expression, e.g., they are STRO-3+ (TNAP+).

Reference to selection of a cell or population thereof does not require selection from a specific tissue source. As described herein STRO-1+ cells can be selected from or isolated from or enriched from a large variety of sources. That said, in some examples, these terms provide support for selection from any tissue comprising STRO-1+ cells (e.g., MPCs) or vascularized tissue or tissue comprising pericytes (e.g., STRO-1+ pericytes) or any one or more of the tissues recited herein.

In one example, the cells used in methods of the present disclosure express one or more markers individually or collectively selected from the group consisting of TNAP+, VCAM-1+, THY-1+, STRO-2+, STRO-4+ (HSP-90β), CD45+, CD146+, 3G5+ or any combination thereof.

By "individually" is meant that the disclosure encompasses the recited markers or groups of markers separately, and that, notwithstanding that individual markers or groups of markers may not be separately listed herein the accompanying claims may define such marker or groups of markers separately and divisibly from each other.

By "collectively" is meant that the disclosure encompasses any number or combination of the recited markers or groups of peptides, and that, notwithstanding that such numbers or combinations of markers or groups of markers may not be specifically listed herein the accompanying claims may define such combinations or sub-combinations separately and divisibly from any other combination of markers or groups of markers.

For example, the STRO-1$^+$ cells are STRO-1$^{bright}$ (syn. STRO-1$^{br}$). In one example, the Stro-1$^{bri}$ cells are preferentially enriched relative to STRO-1$^{dim}$ or STRO-rtermedi$^a_{te}$ cells.

In one example, the STRO-1$^{bright}$ cells are additionally one or more of TNAP$^+$, VCAM-1$^+$, THY-1$^{+'}$ STRO-2$^+$, STRO-4$^+$ (HSP-90P) and/or CD146$^+$. For example, the cells are selected for one or more of the foregoing markers and/or shown to express one or more of the foregoing markers. In this regard, a cell shown to express a marker need not be specifically tested, rather previously enriched or isolated cells can be tested and subsequently used, isolated or enriched cells can be reasonably assumed to also express the same marker.

In one example, the mesenchymal precursor cells are perivascular mesenchymal precursor cells as defined in WO 2004/85630.

A cell that is referred to as being "positive" for a given marker it may express either a low (lo or dim) or a high (bright, bri) level of that marker depending on the degree to which the marker is present on the cell surface, where the terms relate to intensity of fluorescence or other marker used in the sorting process of the cells. The distinction of lo (or dim or dull) and bri will be understood in the context of the marker used on a particular cell population being sorted. A cell that is referred to as being "negative" for a given marker is not necessarily completely absent from that cell. This term means that the marker is expressed at a relatively very low level by that cell, and that it generates a very low signal when detectably labeled or is undetectable above background levels, e.g., levels detected suing an isotype control antibody.

The term "bright", when used herein, refers to a marker on a cell surface that generates a relatively high signal when detectably labeled. Whilst not wishing to be limited by theory, it is proposed that "bright" cells express more of the target marker protein (for example the antigen recognized by STRO-1) than other cells in the sample. For instance, STRO-1$^{bri}$ cells produce a greater fluorescent signal, when labeled with a FITC-conjugated STRO-1 antibody as determined by fluorescence activated cell sorting (FACS) analysis, than non-bright cells (STRO-1$^{dull/dim}$). In one example, "bright" cells constitute at least about 0.1% of the most brightly labeled bone marrow mononuclear cells contained in the starting sample. In other examples, "bright" cells constitute at least about 0.1%, at least about 0.5%, at least about 1%, at least about 1.5%, or at least about 2%, of the most brightly labeled bone marrow mononuclear cells contained in the starting sample. In one example, STRO-1$^{bright}$ cells have 2 log magnitude higher expression of STRO-1 surface expression relative to "background", namely cells that are STRO-1$^-$. By comparison, STRO-1$^{dim}$ and/or $_{STRO}$-1$^{intermediate}$ cells have less than 2 log magnitude higher expression of STRO-1 surface expression, typically about 1 log or less than "background".

As used herein the term "TNAP" is intended to encompass all isoforms of tissue non-specific alkaline phosphatase. For example, the term encompasses the liver isoform (LAP), the bone isoform (BAP) and the kidney isoform (KAP). In one example, the TNAP is BAP. In one example, TNAP as used herein refers to a molecule which can bind the STRO-3 antibody produced by the hybridoma cell line deposited with ATCC on 19 Dec. 2005 under the provisions of the Budapest Treaty under deposit accession number PTA-7282.

Furthermore, in a preferred example, the STRO-1$^+$ cells are capable of giving rise to clonogenic CFU-F.

It is preferred that a significant proportion of the STRO-1$^+$ multipotential cells are capable of differentiation into at least two different germ lines. Non-limiting examples of the lineages to which the multipotential cells may be committed include bone precursor cells; hepatocyte progenitors, which are multipotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other lineages include, but are not limited to, odontoblasts, dentin-producing cells and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells.

In another example, the STRO-1$^+$ cells are not capable of giving rise, upon culturing, to hematopoietic cells.

In one example, the cells are taken from the subject to be treated, cultured in vitro using standard techniques and used to obtain supernatant or soluble factors or expanded cells for administration to the subject as an autologous or allogeneic composition. In an alternative example, cells of one or more of the established human cell lines are used. In another useful example of the disclosure, cells of a non-human animal (or if the patient is not a human, from another species) are used.

The present disclosure also contemplates use of supernatant or soluble factors obtained or derived from STRO-1$^+$ cells and/or progeny cells thereof (the latter also being referred to as expanded cells) which are produced from in vitro culture. Expanded cells of the disclosure may a have a wide variety of phenotypes depending on the culture conditions (including the number and/or type of stimulatory factors in the culture medium), the number of passages and the like. In certain examples, the progeny cells are obtained after about 2, about 3, about 4, about 5, about 6, about 7, about 8, about 9, or about 10 passages from the parental population. However, the progeny cells may be obtained after any number of passages from the parental population.

The progeny cells may be obtained by culturing in any suitable medium. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatin and collagen matrices. Exemplary gaseous media include the gaseous phase that cells growing on a petri dish or other solid or semisolid support are exposed to. The term "medium" also refers to material that is intended for use in a cell culture, even if it has not yet been contacted with cells. In other words, a nutrient rich liquid prepared for bacterial culture is a medium. A powder mixture that when mixed with water or other liquid becomes suitable for cell culture may be termed a "powdered medium".

In an example, progeny cells useful for the methods of the disclosure are obtained by isolating TNAP$^+$ STRO-1$^+$ cells from bone marrow using magnetic beads labeled with the STRO-3 antibody, and then culture expanding the isolated cells (see Gronthos et al. *Blood* 85: 929-940, 1995 for an example of suitable culturing conditions).

In one example, such expanded cells (progeny) (for example, after at least 5 passages) can be TNAP$^-$, CC9$^+$, HLA class I$^+$, HLA class II$^-$, CD$_{14}^-$, CD$_{19}^-$, CD$_3^-$, CD11a$^-$c$^-$, CD31$^-$, CD86$^-$, CD34$^-$ and/or CD80$^-$. However, it is possible that under different culturing conditions to those described herein that the expression of different markers may vary. Also, whilst cells of these phenotypes may predominate in the expended cell population it does not mean that there is a minor proportion of the cells do not have this phenotype(s) (for example, a small percentage of the expanded cells may be CC9$^-$). In one example, expanded cells still have the capacity to differentiate into different cell types.

In one example, an expended cell population used to obtain supernatant or soluble factors, or cells per se, comprises cells wherein at least 25%, e.g., at least 50%, of the cells are CC9$^+$.

In another example, an expanded cell population used to obtain supernatant or soluble factors, or cells per se, comprises cells wherein at least 40%, e.g., at least 45%, of the cells are STRO-1$^+$.

In a further example, the expanded cells may express one or more markers collectively or individually selected from the group consisting of LFA-3, THY-1, VCAM-1, ICAM-1, PECAM-1, P-selectin, L-selectin, 3G5, CD49a/CD49b/CD29, CD49c/CD29, CD49d/CD29, CD 90, CD29, CD18, CD61, integrin beta 6-19, thrombomodulin, CD 10, CD 13, SCF, PDGF-R, EGF-R, IGF1-R, NGF-R, FGF-R, Leptin-R (STRO-2=Leptin-R), RANKL, STRO-4 (HSP-90P), STRO-1$^{bright}$ and CD 146 or any combination of these markers.

In one example, the progeny cells are Multipotential Expanded STRO-1$^+$ Multipotential cells Progeny (MEMPs) as defined and/or described in WO 2006/032092. Methods for preparing enriched populations of STRO-1$^+$ multipotential cells from which progeny may be derived are described in WO 01/04268 and WO 2004/085630. In an in vitro context STRO-1$^+$ multipotential cells will rarely be present as an absolutely pure preparation and will generally be present with other cells that are tissue specific committed cells (TSCCs). WO 01/04268 refers to harvesting such cells from bone marrow at purity levels of about 0.1% to 90%. The population comprising MPCs from which progeny are derived may be directly harvested from a tissue source, or alternatively it may be a population that has already been expanded ex vivo.

For example, the progeny may be obtained from a harvested, unexpanded, population of substantially purified STRO-1$^+$ multipotential cells, comprising at least about 0.1, 1, 5, 10, 20, 30, 40, 50, 60, 70, 80 or 95% of total cells of the population in which they are present. This level may be achieved, for example, by selecting for cells that are positive for at least one marker individually or collectively selected from the group consisting of TNAP, STRO-4 (HSP-90P), STRO-1$^{bright}$ 3G5$^+$, VCAM-1, THY-1, CD 146 and STRO-2.

MEMPS can be distinguished from freshly harvested STRO-1$^+$ multipotential cells in that they are positive for the marker STRO-1$^{bri}$ and negative for the marker Alkaline phosphatase (ALP). In contrast, freshly isolated STRO-1$^+$ multipotential cells are positive for both STRO-1$^{bri}$ and ALP. In one example of the present disclosure, at least 15%, 20%, 30%, 40%, 50%, 60%, 70%, 80%, 90% or 95% of the administered cells have the phenotype STRO-1$^{bri}$, ALP$^-$. In a further example the MEMPS are positive for one or more of the markers Ki67, CD44 and/or CD49c/CD29, VLA-3, $\alpha 3\beta_1$. In yet a further example the MEMPs do not exhibit TERT activity and/or are negative for the marker CD 18.

The STRO-1$^+$ cell starting population may be derived from any one or more tissue types set out in WO 01/04268 or WO 2004/085630, namely bone marrow, dental pulp cells, adipose tissue and skin, or perhaps more broadly from adipose tissue, teeth, dental pulp, skin, liver, kidney, heart, retina, brain, hair follicles, intestine, lung, spleen, lymph node, thymus, pancreas, bone, ligament, bone marrow, tendon and skeletal muscle.

It will be understood that in performing methods described in the present disclosure, separation of cells carrying any given cell surface marker can be effected by a number of different methods, however, exemplary methods rely upon binding a binding agent (e.g., an antibody or antigen binding fragment thereof) to the marker concerned followed by a separation of those that exhibit binding, being either high level binding, or low level binding or no binding. The most convenient binding agents are antibodies or antibody-based molecules, for example monoclonal antibodies or based on monoclonal antibodies (e.g., proteins comprising antigen binding fragments thereof) because of the specificity of these latter agents. Antibodies can be used for both steps, however other agents might also be used, thus ligands for these markers may also be employed to enrich for cells carrying them, or lacking them.

The antibodies or ligands may be attached to a solid support to allow for a crude separation. For example, the separation techniques maximize the retention of viability of the fraction to be collected. Various techniques of different efficacy may be employed to obtain relatively crude separations. The particular technique employed will depend upon efficiency of separation, associated cytotoxicity, ease and speed of performance, and necessity for sophisticated equipment and/or technical skill Procedures for separation may include, but are not limited to, magnetic separation, using antibody-coated magnetic beads, affinity chromatography and "panning" with antibody attached to a solid matrix. Techniques providing accurate separation include but are not limited to FACS. Methods for performing FACS will be apparent to the skilled artisan.

Antibodies against each of the markers described herein are commercially available (e.g., monoclonal antibodies against STRO-1 are commercially available from R&D Systems, USA), available from ATCC or other depositary organization and/or can be produced using art recognized techniques.

In one example, the method for isolating STRO-1$^+$ cells comprises a first step being a solid phase sorting step utilizing for example magnetic activated cell sorting (MACS) recognizing high level expression of STRO-1. A second sorting step can then follow, should that be desired, to result in a higher level of precursor cell expression as described in patent specification WO 01/14268. This second sorting step might involve the use of two or more markers.

The method obtaining STRO-1$^+$ cells might also include the harvesting of a source of the cells before the first enrichment step using known techniques. Thus the tissue will be surgically removed. Cells comprising the source tissue will then be separated into a so called single cells suspension. This separation may be achieved by physical and or enzymatic means.

Once a suitable STRO-1+ cell population has been obtained, it may be cultured or expanded by any suitable means to obtain MEMPs.

In one example, the cells are taken from the subject to be treated, cultured in vitro using standard techniques and used to obtain supernatant or soluble factors or expanded cells for administration to the subject as an autologous or allogeneic composition. In an alternative example, cells of one or more of the established human cell lines are used to obtain the supernatant or soluble factors. In another useful example of the disclosure, cells of a non-human animal (or if the patient is not a human, from another species) are used to obtain supernatant or soluble factors.

Methods and uses of the present disclosure can be practiced using cells from any non-human animal species, including but not limited to non-human primate cells, ungulate, canine, feline, lagomorph, rodent, avian, and fish cells. Primate cells with which methods of the disclosure may be performed include but are not limited to cells of chimpanzees, baboons, cynomolgus monkeys, and any other New or Old World monkeys. Ungulate cells with which the disclosure may be performed include but are not limited to cells of bovines, porcines, ovines, caprines, equines, buffalo and bison. Rodent cells with which the disclosure may be performed include but are not limited to mouse, rat, guinea pig, hamster and gerbil cells. Examples of lagomorph species with which the disclosure may be performed include domesticated rabbits, jack rabbits, hares, cottontails, snowshoe rabbits, and pikas. Chickens (*Gallus gallus*) are an example of an avian species with which methods of the disclosure may be performed.

In one example, the cells are human cells.

Cells useful for the methods of the disclosure may be stored before use, or before obtaining the supernatant or soluble factors. Methods and protocols for preserving and storing of eukaryotic cells, and in particular mammalian cells, are known in the art (cf, for example, Pollard, J. W. and Walker, J. M. (1997) Basic Cell Culture Protocols, Second Edition, Humana Press, Totowa, N.J.; Freshney, R. I. (2000) Culture of Animal Cells, Fourth Edition, Wiley-Liss, Hoboken, N.J.). Any method maintaining the biological activity of the isolated stem cells such as mesenchymal stem/progenitor cells, or progeny thereof, may be utilized in connection with the present disclosure. In one example, the cells are maintained and stored by using cryo-preservation.

Genetically-Modified Cells

In one example, the STRO-1+ cells and/or progeny cells thereof are genetically modified, e.g., to express and/or secrete a protein of interest. For example, the cells are engineered to express a protein useful in the treatment of metabolic syndrome or obesity, such as, glucagon like protein-1 (GLP-1) or peptide YY (PYY) or active fragments thereof (e.g., PYY[3-36]), exendin-4 or Exenatide.

Methods for genetically modifying a cell will be apparent to the skilled artisan. For example, a nucleic acid that is to be expressed in a cell is operably-linked to a promoter for inducing expression in the cell. For example, the nucleic acid is linked to a promoter operable in a variety of cells of a subject, such as, for example, a viral promoter, e.g., a CMV promoter (e.g., a CMV-IE promoter) or a SV-40 promoter. Additional suitable promoters are known in the art and shall be taken to apply mutatis mutandis to the present example of the disclosure.

In one example, the nucleic acid is provided in the form of an expression construct. As used herein, the term "expression construct" refers to a nucleic acid that has the ability to confer expression on a nucleic acid (e.g. a reporter gene and/or a counter-selectable reporter gene) to which it is operably connected, in a cell. Within the context of the present disclosure, it is to be understood that an expression construct may comprise or be a plasmid, bacteriophage, phagemid, cosmid, virus sub-genomic or genomic fragment, or other nucleic acid capable of maintaining and/or replicating heterologous DNA in an expressible format.

Methods for the construction of a suitable expression construct for performance of the disclosure will be apparent to the skilled artisan and are described, for example, in Ausubel et al (In: Current Protocols in Molecular Biology. Wiley Interscience, ISBN 047 150338, 1987) or Sambrook et al (In: Molecular Cloning: Molecular Cloning: A Laboratory Manual, Cold Spring Harbor Laboratories, New York, Third Edition 2001). For example, each of the components of the expression construct is amplified from a suitable template nucleic acid using, for example, PCR and subsequently cloned into a suitable expression construct, such as for example, a plasmid or a phagemid.

Vectors suitable for such an expression construct are known in the art and/or described herein. For example, an expression vector suitable for methods of the present disclosure in a mammalian cell is, for example, a vector of the pcDNA vector suite supplied by Invitrogen, a vector of the pCI vector suite (Promega), a vector of the pCMV vector suite (Clontech), a pM vector (Clontech), a pSI vector (Promega), a VP 16 vector (Clontech) or a vector of the pcDNA vector suite (Invitrogen).

The skilled artisan will be aware of additional vectors and sources of such vectors, such as, for example, Life Technologies Corporation, Clontech or Promega.

Means for introducing the isolated nucleic acid molecule or a gene construct comprising same into a cell for expression are known to those skilled in the art. The technique used for a given organism depends on the known successful techniques. Means for introducing recombinant DNA into cells include microinjection, transfection mediated by DEAE-dextran, transfection mediated by liposomes such as by using lipofectamine (Gibco, Md., USA) and/or cellfectin (Gibco, Md., USA), PEG-mediated DNA uptake, electroporation and microparticle bombardment such as by using DNA-coated tungsten or gold particles (Agracetus Inc., WI, USA) amongst others.

Alternatively, an expression construct of the disclosure is a viral vector. Suitable viral vectors are known in the art and commercially available. Conventional viral-based systems for the delivery of a nucleic acid and integration of that nucleic acid into a host cell genome include, for example, a retroviral vector, a lentiviral vector or an adeno-associated viral vector. Alternatively, an adenoviral vector is useful for introducing a nucleic acid that remains episomal into a host cell. Viral vectors are an efficient and versatile method of gene transfer in target cells and tissues. Additionally, high transduction efficiencies have been observed in many different cell types and target tissues.

For example, a retroviral vector generally comprises cis-acting long terminal repeats (LTRs) with packaging capacity for up to 6-10 kb of foreign sequence. The minimum cis-acting LTRs are sufficient for replication and packaging of a vector, which is then used to integrate the expression construct into the target cell to provide long term expression. Widely used retroviral vectors include those based upon murine leukemia virus (MuLV), gibbon ape leukemia virus (GaLV), simian immunodeficiency virus (SrV), human immunodeficiency virus (HIV), and combinations thereof (see, e.g., Buchscher et al, *J. Virol.* 56:2731-2739 (1992); Johann et al, *J. Virol* 65:1635-1640 (1992); Sommerfelt et al, Virol 76:58-59 (1990); Wilson et al, *J. Virol* 63:274-2318 (1989); Miller et al, *J. Virol* 65:2220-2224 (1991); PCT/US94/05700; Miller and Rosman *BioTechniques* 7:980-990, 1989; Miller, A. D. *Human Gene Therapy* 7:5-14, 1990; Scarpa et al *Virology* 75:849-852, 1991; Burns et al. *Proc. Natl Acad. Sci USA* 90:8033-8037, 1993).

Various adeno-associated virus (AAV) vector systems have also been developed for nucleic acid delivery. AAV vectors can be readily constructed using techniques known in the art. See, e.g., U.S. Pat. Nos. 5,173,414 and 5,139,941; International Publication Nos. WO 92/01070 and WO 93/03769; Lebkowski et al *Molec. Cell Biol* 5:3988-3996, 1988; Vincent et al. (1990) Vaccines 90 (Cold Spring Harbor Laboratory Press); Carter *Current Opinion in Biotechnology* 5:533-539, 1992; Muzyczka. *Current Topics in Microbiol, and Immunol.* 755:97-129, 1992; Kotin, Human Gene Therapy 5:793-801, 1994; Shelling and Smith *Gene Therapy* 7:165-169, 1994; and Zhou et al *J Exp. Med.* 779:1867-1875, 1994.

Additional viral vectors useful for delivering an expression construct of the disclosure include, for example, those derived from the pox family of viruses, such as vaccinia virus and avian poxvirus or an alphavirus or a conjugate virus vector (e.g. that described in Fisher-Hoch et al, *Proc. Natl Acad. Sci. USA* 56:317-321, 1989).

Assaying Therapeutic/Prophylactic Potential of Cells and Soluble Factors

Methods for determining the ability of cells or soluble factors to treat or prevent or delay the onset or progression of metabolic syndrome or obesity will be apparent to the skilled artisan.

For example, cells or soluble factors (e.g., a mixture of factors or a single factor or a fraction of factors (e.g., derived by affinity purification or chromatography)) are administered to a model of metabolic syndrome and/or obesity and the effect on one or more symptoms is assessed.

Exemplary models of metabolic syndrome include high fat fed KK/Ta mice (Akagiri et al, *J Clin Biochem Nutr.* 42: 150-157, 2008), C57Bl/6NCrl-Lepr$^{db/db}$/Crl mice (Charles River Laboratories), high fructose fed rodents (Le and Tappy, *Current Opinion in Clinical Nutrition and Metabolic Care*, 9: 469^175, 2006), high sucrose fed rats (Coelho et al, *Regulatory Peptides*, 162: 61-67, 2010), high fat fed rodents, and high fat and high carbohydrate fed rodents (e.g., as reviewed in Panchal and Brown, *Journal of Biomedicine and Biotechnology* (2011).

Exemplary genetic models of obesity include dbldb mice, obiob mice, Zucker diabetic fatty rats and Otsuka Long-Evans Tokushima Fatty rats.

Exemplary induced models of obesity include high fat fed rodents and/or high fat and high carbohydrate fed rodents.

In one example, a model of metabolic syndrome and/or obesity is a high fat fed non-human primate, e.g., cynomolgus monkeys).

It will be apparent to the skilled artisan from the foregoing that the present disclosure also provides a method for identifying or isolating a cell or a soluble factor for the treatment, prevention or delay of metabolic syndrome or obesity, the method comprising:
(i) administering a cell or a soluble factor to a test subject suffering from metabolic syndrome and/or obesity and assessing a symptom of metabolic syndrome and/or body weight in the subject;
(ii) comparing the symptom of metabolic syndrome and/or body weight levels of the subject at (i) to the symptom of metabolic syndrome and/or body weight of a control subject suffering from the metabolic syndrome and/or obesity to which the cell or soluble factor has not been administered, wherein an improvement in the symptom and/or reduced body weight in the test subject compared to the control subject indicates that the cell or soluble factor treats metabolic syndrome and/or obesity thereof.

The cell may be any cell described herein according to any example.

Exemplary symptoms are described herein.

Cellular Compositions

In one example of the present disclosure STRO-1$^+$ cells and/or progeny cells thereof are administered in the form of a composition. In one example, such a composition comprises a pharmaceutically acceptable carrier and/or excipient.

The terms "carrier" and "excipient" refer to compositions of matter that are conventionally used in the art to facilitate the storage, administration, and/or the biological activity of an active compound (see, e.g., Remington's Pharmaceutical Sciences, 16th Ed., Mac Publishing Company (1980). A carrier may also reduce any undesirable side effects of the active compound. A suitable carrier is, for example, stable, e.g., incapable of reacting with other ingredients in the carrier. In one example, the carrier does not produce significant local or systemic adverse effect in recipients at the dosages and concentrations employed for treatment.

Suitable carriers for the present disclosure include those conventionally used, e.g., water, saline, aqueous dextrose, lactose, Ringer's solution, a buffered solution, hyaluronan and glycols are exemplary liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

In another example, a carrier is a media composition, e.g., in which a cell is grown or suspended. For example, such a media composition does not induce any adverse effects in a subject to whom it is administered.

Exemplary carriers and excipients do not adversely affect the viability of a cell and/or the ability of a cell to reduce, prevent or delay metabolic syndrome and/or obesity.

In one example, the carrier or excipient provides a buffering activity to maintain the cells and/or soluble factors at a suitable pH to thereby exert a biological activity, e.g., the carrier or excipient is phosphate buffered saline (PBS). PBS represents an attractive carrier or excipient because it interacts with cells and factors minimally and permits rapid release of the cells and factors, in such a case, the composition of the disclosure may be produced as a liquid for direct application to the blood stream or into a tissue or a region surrounding or adjacent to a tissue, e.g., by injection.

STPvO-1$^+$ cells and/or progeny cells thereof can also be incorporated or embedded within scaffolds that are recipient-compatible and which degrade into products that are not harmful to the recipient. These scaffolds provide support and protection for cells that are to be transplanted into the recipient subjects. Natural and/or synthetic biodegradable scaffolds are examples of such scaffolds.

A variety of different scaffolds may be used successfully in the practice of methods of the disclosure. Exemplary scaffolds include, but are not limited to biological, degradable scaffolds. Natural biodegradable scaffolds include collagen, fibronectin, and laminin scaffolds. Suitable synthetic material for a cell transplantation scaffold should be able to support extensive cell growth and cell function. Such scaffolds may also be resorbable. Suitable scaffolds include polyglycolic acid scaffolds, e.g., as described by Vacanti, et al. *J. Ped. Surg.* 23:3-9 1988; Cima, et al. *Biotechnol. Bioeng.* 35:145 1991;

Vacanti, et al. *Plast. Reconstr. Surg.* 88:753-9 1991; or synthetic polymers such as polyanhydrides, polyorthoesters, and polylactic acid.

In another example, the cells may be administered in a gel scaffold (such as Gelfoam from Upjohn Company.

The cellular compositions useful for methods described herein may be administered alone or as admixtures with other cells. Cells that may be administered in conjunction with the compositions of the present disclosure include, but are not limited to, other multipotent or pluripotent cells or stem cells, or bone marrow cells. The cells of different types may be admixed with a composition of the disclosure immediately or shortly prior to administration, or they may be co-cultured together for a period of time prior to administration.

In one example, the composition comprises an effective amount or a therapeutically or prophylactically effective amount of cells. For example, the composition comprises about $1 \times 10^5$ STRO-$1^+$ cells/kg to about $1 \times 10^7$ STRO-$1^+$ cells/kg or about $1 \times 10^6$ STRO-$1^+$ cells/kg to about $5 \times 10^6$ STRO-$1^+$ cells/kg. The exact amount of cells to be administered is dependent upon a variety of factors, including the age, weight, and sex of the patient, and the extent and severity of the metabolic syndrome and/or obesity.

In one example, a low dose of cells is administered to the subject. Exemplary dosages include between about $0.1 \times 10^4$ and $0.5 \times 10^6$ cells per kg, for example, between about $0.1 \times 10^5$ and $0.5 \times 10^6$ cells per kg, such as, between about $0.5 \times 10^5$ and $0.5 \times 10^6$ cells per kg, for example, between about $0.1 \times 10^6$ and $0.5 \times 10^6$ cells per kg, e.g., about $0.2 \times 10^6$ or $0.3 \times 10^6$ or $0.4 \times 10^6$ cells per kg.

In some examples, cells are contained within a chamber that does not permit the cells to exit into a subject's circulation, however that permits factors secreted by the cells to enter the circulation. In this manner soluble factors may be administered to a subject by permitting the cells to secrete the factors into the subject's circulation. Such a chamber may equally be implanted at a site in a subject to increase local levels of the soluble factors, e.g., implanted in or near a pancreas.

In some examples of the disclosure, it may not be necessary or desirable to immunosuppress a patient prior to initiation of therapy with cellular compositions. Accordingly, transplantation with allogeneic, or even xenogeneic, STRO-$1^+$ cells or progeny thereof may be tolerated in some instances.

However, in other instances it may be desirable or appropriate to pharmacologically immunosuppress a patient prior to initiating cell therapy and/or reduce an immune response of a subject against the cellular composition. This may be accomplished through the use of systemic or local immunosuppressive agents, or it may be accomplished by delivering the cells in an encapsulated device. The cells may be encapsulated in a capsule that is permeable to nutrients and oxygen required by the cell and therapeutic factors the cell is yet impermeable to immune humoral factors and cells. For example, the encapsulant is hypoallergenic, is easily and stably situated in a target tissue, and provides added protection to the implanted structure. These and other means for reducing or eliminating an immune response to the transplanted cells are known in the art. As an alternative, the cells may be genetically modified to reduce their immunogenicity.

Compositions of Soluble Factors

In one example, STRO-$1^+$ cell-derived and/or progeny cell-derived supernatant or soluble factors are administered in the form of a composition, e.g., comprising a suitable carrier and/or excipient. In one example, the carrier or excipient does not adversely affect the biological effect of the soluble factors or supernatant.

In one example, the composition comprises a composition of matter to stabilize a soluble factor or a component of supernatant, e.g., a protease inhibitor. In one example, the protease inhibitor is not included in an amount sufficient to have an adverse effect on a subject.

Compositions comprising STRO-$1^+$ cell-derived and/or progeny cell-derived supernatant or soluble factors may be prepared as appropriate liquid suspensions, e.g., in culture medium or in a stable carrier or a buffer solution, e.g., phosphate buffered saline. Suitable carriers are described herein above. In another example, suspensions comprising STRO-$1^+$ cell-derived and/or progeny cell-derived supernatant or soluble factors are oily suspensions for injection. Suitable lipophilic solvents or vehicles include fatty oils such as sesame oil; or synthetic fatty acid esters, such as ethyl oleate or triglycerides; or liposomes. Suspensions to be used for injection may also contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Sterile injectable solutions can be prepared by incorporating the supernatant or soluble factors in the required amount in an appropriate solvent with one or a combination of ingredients described above, as required, followed by filtered sterilization.

Generally, dispersions are prepared by incorporating the supernatant or soluble factors into a sterile vehicle that contains a basic dispersion medium and the required other ingredients from those enumerated above. In the case of sterile powders for the preparation of sterile injectable solutions, exemplary methods of preparation are vacuum drying and freeze-drying which yields a powder of the active ingredient plus any additional desired ingredient from a previously sterile-filtered solution thereof. In accordance with an alternative example of the disclosure, the supernatant or soluble factors may be formulated with one or more additional compounds that enhance its solubility.

Other exemplary carriers or excipients are described, for example, in Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.

Therapeutic compositions typically should be sterile and stable under the conditions of manufacture and storage. The composition can be formulated as a solution, microemulsion, liposome, or other ordered structure. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In some cases, isotonic agents, for example, sugars, polyalcohols such as mannitol, sorbitol, or sodium chloride are included in the composition. Prolonged absorption of the injectable compositions can be brought about by including in the composition an agent which delays absorption, for example, monostearate salts and gelatin. Moreover, the soluble factors may be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

The supernatant or soluble factors may be administered in combination with an appropriate matrix, for instance, to provide slow release of the soluble factors.

Additional Components of Compositions

The STRO-1$^+$ cell-derived supernatant or soluble factors, STRO-1$^+$ cells or progeny thereof may be administered with other beneficial drugs or biological molecules (growth factors, trophic factors). When administered with other agents, they may be administered together in a single pharmaceutical composition, or in separate pharmaceutical compositions, simultaneously or sequentially with the other agents (either before or after administration of the other agents). Bioactive factors which may be co-administered include anti-apoptotic agents (e.g., EPO, EPO mimetibody, TPO, IGF-I and IGF-II, HGF, caspase inhibitors); anti-inflammatory agents (e.g., p38 MAPK inhibitors, TGF-beta inhibitors, statins, IL-6 and IL-1 inhibitors, PEMIROLAST, TRANILAST, REMICADE, SIROLIMUS, and NSAIDs (non-steroidal anti-inflammatory drugs; e.g., TEPDXALIN, TOLMETIN, SUPROFEN); immunosupressive/immunomodulatory agents (e.g., calcineurin inhibitors, such as cyclosporine, tacrolimus; mTOR inhibitors (e.g., SIROLIMUS, EVEROLIMUS); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti-lymphocyte globulin (ALG); monoclonal anti-T cell antibody OKT3)); anti-thrombogenic agents (e.g., heparin, heparin derivatives, urokinase, PPack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine) as well as local anesthetics.

In one example, a composition as described herein according to any example comprises an additional factor for the treatment or prophylaxis of metabolic syndrome and/or obesity, e.g., as described herein, such as a statin.

Alternatively, or in addition, cells, secreted factors and/or a composition as described herein according to any example is combined with a known treatment of metabolic syndrome and/or obesity.

In one example, a pharmaceutical composition as described herein according to any example comprises a compound used to treat metabolic syndrome and/or obesity. Alternatively, a method of treatment/prophylaxis as described herein according to any example of the disclosure additionally comprises administering a compound used to treat metabolic syndrome and/or obesity. Exemplary compounds are described herein and are to be taken to apply mutatis mutandis to these examples of the present disclosure.

In another example, a composition as described herein according to any example additionally comprises a factor that induces or enhances differentiation of a progenitor cell into a vascular cell. Exemplary factors include, vascular endothelial growth factor (VEGF), platelet derived growth factor (PDGF; e.g., PDGF-BB), and FGF.

In another example, a composition as described herein according to any example additionally comprises a tissue specific committed cell (TSCC). In this respect, International Patent Application No. PCT/AU2005/001445 demonstrates that administration of a TSCC and a STRO-1$^+$ cells can lead to enhanced proliferation of the TSCC. In one example, the TSCC is a vascular cell. Administration of such a composition to a subject may lead to increased production of vasculature, e.g., leading to increased nutrients being delivered to the affected tissue.

Medical Devices

The present disclosure also provides medical devices for use or when used in a method as described herein according to any example. For example, the present disclosure provides a syringe or catheter or other suitable delivery device comprising STRO-1$^+$ cells and/or progeny cells thereof and/or soluble factors therefrom and/or a composition as described herein according to any example. Optionally, the syringe or catheter is packaged with instructions for use in a method as described herein according to any example.

In another example, the present disclosure provides an implant comprising STRO-1$^+$ cells and/or progeny cells thereof and/or soluble factors therefrom and/or a composition as described herein according to any example. Optionally, the implant is packaged with instructions for use in a method as described herein according to any example. Suitable implants may be formed with a scaffold, e.g., as described herein above and STRO-1$^+$ cells and/or progeny cells thereof and/or soluble factors therefrom.

Modes of Administration

The STRO-1$^+$ cell-derived supernatant or soluble factors, STRO-1$^+$ cells or progeny thereof may be surgically implanted, injected, delivered (e.g., by way of a catheter or syringe), or otherwise administered directly or indirectly to the site in need of repair or augmentation, e.g., into a fat pad.

In on example, the STRO-1$^+$ cell-derived supernatant or soluble factors, STRO-1$^+$ cells or progeny thereof is/are delivered to the blood stream of a subject. For example, the STRO-1$^+$ cell-derived supernatant or soluble factors, STRO-1$^+$ cells or progeny thereof are delivered parenterally. Exemplary routes of parenteral administration include, but are not limited to, intraperitoneal, intraventricular, intracerebroventricular, intrathecal, or intravenous. In one example, the STRO-1$^+$ cell-derived supernatant or soluble factors, STRO-1$^+$ cells or progeny thereof are delivered intra-arterially, into an aorta, into an atrium or ventricle of the heart or into a blood vessel, e.g., intravenously.

In the case of cell delivery to an atrium or ventricle of the heart, cells can be administered to the left atrium or ventricle to avoid complications that may arise from rapid delivery of cells to the lungs.

In one example, the STRO-1$^+$ cell-derived supernatant or soluble factors, STRO-1$^+$ cells or progeny thereof are delivered intravenously.

In one example, the STRO-1$^+$ cell-derived supernatant or soluble factors, STRO-1$^+$ cells or progeny thereof are injected into the site of delivery, e.g., using a syringe or through a catheter or a central line.

Selecting an administration regimen for a therapeutic formulation depends on several factors, including the serum or tissue turnover rate of the entity, the level of symptoms, and the immunogenicity of the entity. In one example, an administration regimen maximizes the amount of therapeutic compound delivered to the patient consistent with an acceptable level of side effects. Accordingly, the amount of formulation delivered depends in part on the particular entity and the severity of the condition being treated.

In one example, STRO-1$^+$ cell-derived supernatant or soluble factors, STRO-1$^+$ cells or progeny thereof are delivered as a single bolus dose. Alternatively, STRO-1$^+$ cell-derived supernatant or soluble factors, STRO-1$^+$ cells or progeny thereof are administered by continuous infusion, or by doses at intervals of, e.g., one day, one week, or 1-7 times per week. An exemplary dose protocol is one involving the maximal dose or dose frequency that avoids significant undesirable side effects. A total weekly dose depends on the type and activity of the compound/cell being used. Determination of the appropriate dose is made by a clinician, e.g., using parameters or factors known or suspected in the art to affect treatment or predicted to affect treatment. Generally, the dose begins with an amount somewhat less than the optimum dose and is increased by small increments thereafter until the desired or optimum effect is achieved relative to any negative side effects.

The present inventors have shown therapeutic benefits provided by STRO-1$^+$ cells and/or progeny thereof and/or soluble factors derived therefrom are observed for at least four weeks in a subject. Accordingly, in some examples the cells are administered weekly, fortnightly, once every three weeks or once every four weeks.

In accordance with examples of the disclosure directed to treating or delaying the progression of metabolic syndrome and/or obesity, STRO-1$^+$ cells and/or progeny cells thereof and/or soluble factors derived therefrom are administered following diagnosis of the disorder, e.g., using standard methods known in the art and/or described herein.

For those examples directed to preventing or delaying the onset of metabolic syndrome and/or obesity, the STRO-1$^+$ cells and/or progeny cells thereof and/or soluble factors derived therefrom can administered prior to clinical diagnosis of the disorder.

The present disclosure includes the following non-limiting examples.

EXAMPLES

Example 1

Immunoselection of MPCs by Selection of STRO-3$^+$ Cells

Bone marrow (BM) is harvested from healthy normal adult volunteers (20-35 years old). Briefly, 40 ml of BM is aspirated from the posterior iliac crest into lithium-heparin anticoagulant-containing tubes.

BMMNC are prepared by density gradient separation using Lymphoprep™ (Nycomed Pharma, Oslo, Norway) as previously described (Zannettino, A. C. et al. (1998) *Blood* 92: 2613-2628). Following centrifugation at 400×g for 30 minutes at 4° C., the buffy layer is removed with a transfer pipette and washed three times in "HHF", composed of Hank's balanced salt solution (HBSS; Life Technologies, Gaithersburg, Md.), containing 5% fetal calf serum (FCS, CSL Limited, Victoria, Australia).

STRO-3$^+$ (or TNAP$^+$) cells were subsequently isolated by magnetic activated cell sorting as previously described (Gronthos et al. (2003) *Journal of Cell Science* 116: 1827-1835; Gronthos, S. and Simmons, P. J. (1995) *Blood* 85: 929-940). Briefly, approximately 1–3×10$^8$ BMMNC are incubated in blocking buffer, consisting of 10% (v/v) normal rabbit serum in HHF for 20 minutes on ice. The cells are incubated with 200 μl of a 10 μg/ml solution of STRO-3 mAb in blocking buffer for 1 hour on ice. The cells are subsequently washed twice in HHF by centrifugation at 400×g. A 1/50 dilution of goat anti-mouse γ-biotin (Southern Biotechnology Associates, Birmingham, UK) in HHF buffer is added and the cells incubated for 1 hour on ice. Cells are washed twice in MACS buffer (Ca$^{2+}$- and Mn$^{2+}$-free PBS supplemented with 1% BSA, 5 mM EDTA and 0.01% sodium azide) as above and resuspended in a final volume of 0.9 ml MACS buffer.

One hundred μl streptavidin microbeads (Miltenyi Biotec; Bergisch Gladbach, Germany) are added to the cell suspension and incubated on ice for 15 minutes. The cell suspension is washed twice and resuspended in 0.5 ml of MACS buffer and subsequently loaded onto a mini MACS column (MS Columns, Miltenyi Biotec), and washed three times with 0.5 ml MACS buffer to retrieve the cells which did not bind the STRO-3 mAb (deposited on 19 Dec. 2005 with American Type Culture Collection (ATCC) under accession number PTA-7282—see International Publication No. WO 2006/108229). After addition of a further 1 ml MACS buffer, the column is removed from the magnet and the TNAP cells are isolated by positive pressure. An aliquot of cells from each fraction can be stained with streptavidin-FITC and the purity assessed by flow cytometry.

Example 2

Cells Selected by STRO-3 mAb are STRO-1$^{bright}$ Cells

Experiments were designed to confirm the potential of using STRO-3 mAb as a single reagent for isolating cells STRO-1$^{bright}$ cells.

Figure 1:
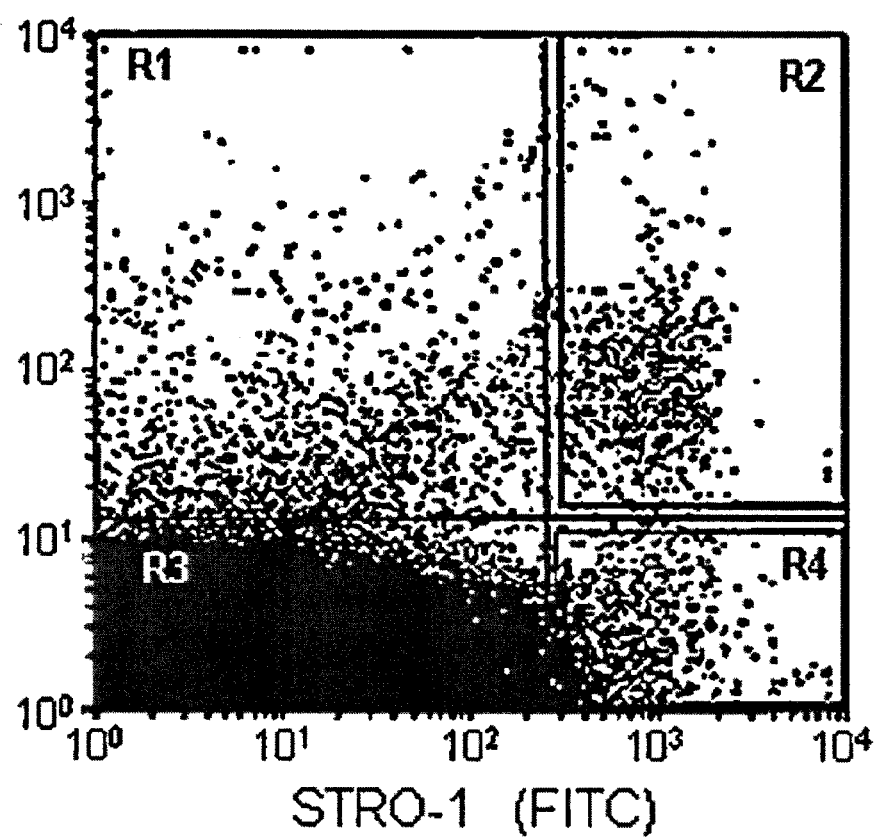
FIG. 1. Co-expression of TNAP (STRO-3) and the Mesenchymal Precursor Cell Marker, STRO-1$^{bright}$ by Adult Human bone marrow morphonuclear cells (BMMNC). Dual-color immunofluorescence and flow cytometry was performed by incubation of STRO-1 MACS-selected BMMNC and indirectly labeled with a goat anti-murine IgM antibody coupled to FITC (x axis), and STRO-3 mAb (murine IgG1) indirectly labeled with a goat anti-murine IgG coupled to PE (y axis). The dot plot histogram represents $5 \times 10^4$ events collected as listmode data. The vertical and horizontal lines were set to the reactivity levels of <1.0% mean fluorescence obtained with the isotype-matched control antibodies, 1B5

Given that STRO-3 (IgG1) is a different isotype to that of STRO-1 (IgM), the ability of STRO-3 to identify clonogenic CFU-F was assessed by two-color FACS analysis based on its co-expression with STRO-1$^-$ cells isolated using the MACS procedure (FIG. 1). The dot plot histogram represents 5×10$^4$ events collected as listmode data. The vertical and horizontal lines were set to the reactivity levels of <1.0% mean fluorescence obtained with the isotype-matched control antibodies, 1B5 (IgG) and 1A6. 12 (IgM) treated under the same conditions. The results demonstrate that a minor population of STRO-1$^{bright}$ cells co-expressed TNAP (upper right quadrant) while the remaining STRO-1$^+$ cells failed to react with the STRO-3 mAb. Cells isolated by FACS from all four quadrants were subsequently assayed for the incidence of CFU-F (Table 1).

TABLE 1

Enrichment of human bone marrow cells by dual-color FACS analysis based on the co-expression of the cell surface markers STRO-1 and TNAP (refer to FIG. 1). FACS sorted cells were cultured under standard clonogenic conditions in alpha MEM supplemented with 20% FCS. The data represents the mean number of day 14 colony-forming cells (CFU-F) per 10$^5$ cells plated ± SE (n = 3 different bone marrow aspirates). These data suggest that human MPC are exclusively restricted to the TNAP positive fraction of BM which co-express the STRO-1 antigen brightly.

| Bone Marrow Fraction | Frequency of CFU-F/10$^5$ Cells | Enrichment (Fold Increase) |
|---|---|---|
| Unfractionated BMMNC | 11.0 ± 2.2 | 1.0 |
| TNAP$^+$/STRO-1$^{bright}$ | 4,511 ± 185 | 410 |
| TNAPVSTRO-1$^{dull}$ | 0.0 | 0.0 |

Example 3

Characterization of Cynomolgus Monkey STRO-3+ MPCs

Simian marrow progenitor cells (from cynomolgus monkeys; cyno-MPC) were isolated from ~15 ml of bone marrow aspirate collected from a female *Macaca fascicularis*. The marrow aspirate suspension was separated using a Ficoll gradient and washed to remove non-nucleated cells (red blood cells). The nucleated cells were counted then separated by attaching CA12 antibody (anti-STRO-3) and Dynalbeads. The cells with antibody and beads attached were positively selected by the magnetic field of an MPC-1 magnet. The positive selected cells were counted and seeded into T-flasks at passage (p.) 0 in Growth Medium. Pre-selection, positive, and negative cells were used in a colony forming assay (CFU-F).

The cyno-MPC cells were fed with Growth Media. All cultures (p.0-p.5) were fed every 2 to 4 days until they reached desired confluence. The cells were then passaged or harvested using HBSS wash and then collagenase followed by Trypsin/Versene. The p. 1 cells were counted and seeded into T-flasks. When the p. 1 cyno-MPC reached desired confluence the cells were harvested and cryopreserved using a controlled rate freezer.

Passage 1 cryopreserved cyno-MPC were thawed and seeded into T-flasks (p. 2). The p. 2 cells were passaged into a Cell Factory at p. 3. The p. 3 cells were harvested and passaged to p. 4 in to a Cell Factory. Extra p. 3 cells were cryopreserved. The p. 4 cells were passaged to 6× Cell Factories at p. 5. When the p. 5 cyno-MPC reached desired confluence the cells were harvested and cryopreserved using a controlled rate freezer. The cells were cryopreserved in 50% AlphaMEM, 42.5% Profreeze, and 7.5% DMSO. Samples were tested for CFU-F assay, FACS, sterility, mycoplasma, and endotoxin.

Results of representative flow cytometry analysis of the immunophenotype of cultured cyno-MPCs are shown in FIG. 2. As shown, these cells are STRO-1+, STRO-4+ and CD146+.

Cyno MPC at p5 were thawed and used for the intravenous injection of diabetic and non-diabetic cynomolgous monkeys as described in Example 4.

Example 4

STRO-3 MPCs are Effective at Treating Metabolic Syndrome and Obesity Even at Low Dosages Five (5) cynomolgous monkeys were selected for treatment. The monkeys had dietary metabolic syndrome (body mass index>35, triglycerides>75 mg/dL and low HDL levels. Monkeys were assessed over a one month period for overt signs of diabetes based on fasting glucose levels, fasting insulin levels, and insulin/glucose response following intravenous glucose tolerance test (IVGTT). Three of the five monkeys were identified as having diabetes (mean monthly fasting glucose>110). Baseline characteristics of the monkeys are shown in Table 2.

TABLE 2

Characteristics of diabetic and non-diabetic animals

| Characteristic | Non-diabetics (n = 2) | Diabetics (n = 3) |
|---|---|---|
| Weight (kg) | 7.8 | 9.0 |
| Fasting glucose (mg/dL) | 92 | 140 |
| Fasting insulin (mU/L) | 45 | 28 |
| Triglycerides (mg/dL) | 25 | 18 |
| Lipoprotein Index | 0.6 | 0.3 |

The monkeys were assigned to Groups 1, 2 or 3 Animals received a single slow intravenous (IV) infusion of allogeneic MPC (isolated as described in Example 2) into the cephalic vein or a suitable peripheral vein at a dose as follows (dose was be adjusted to the latest body weight recorded):

TABLE 3

Summary of treatment groups

| Group | Dose level | Dose MPC/kg | Route |
|---|---|---|---|
| 1 | Low | $0.3 \times 10^6$ | IV |
| 2 | Mid | $1 \times 10^6$ | IV |
| 3 | High | $2 \times 10^6$ | IV |

Three months later monkeys received a second infusion of MPCs at the same dose.

Over the six months following the first infusions, monkeys were assessed bi-weekly for weight, lipid profiles, fasting blood glucose levels, fasting blood insulin levels, and glucose and insulin responses to IVGTT.

Results

FIG. 3 demonstrates that diabetic animals show a defect in late phase insulin response to glucose loading prior to infusion of MPCs.

Results shown in FIG. 4 indicate that in non-diabetic animals the first dose of MPCs induce a modest change in the insulin response and the second dose induced a profound insulin response that sustained for 3 months (i.e., from month 4 to 6). In the diabetic group both the first and second MPC doses sequentially demonstrated increased insulin responses that sustained for 6 months. These data are supportive that MPC are able to improve pancreatic beta-cell function as depicted by the induction of the insulin response after glucose loading in the diabetic and moderately diabetic animals.

Consistent with the individual animal data shown in FIG. 5, the grouped data for non-diabetic animals in FIG. 5 (Panel a) show that the second MPC infusion induced a profound insulin response that was sustained for 3 months (i.e., from month 4 to 6). This is corroborated in FIG. 5 (Panel b) which shows that there is an induction of 50-100% in late phase insulin response after the second MPC infusion.

However, in FIG. 5 (Panel a) the pooled diabetic group data show that both the first and second MPC doses sequentially increased the late phase insulin responses that were sustained for 6 months. A 40-75% and 75-175% increase in late phase insulin responses were observed after the first and second MPC infusions, respectively. These data are supportive that successive doses of MPC induce late phase insulin response after glucose loading.

MPC treatment also produced an increase in the rate of glucose clearance after the first and second MPC treatments in non-diabetic animals (FIG. 6). For example, the second dose induced a sustained response for 3 months (i.e., from month 4 to 6). In addition, in diabetic animals both the first and second MPC doses sequentially demonstrated increased rates of glucose clearance that sustained for 6 months. These data indicate that the induction in late phase insulin response following glucose loading as illustrated in FIGS. 4 and 5 is responsible for the increase in glucose clearance after MPC treatment compared to baseline pretreatment values shown in FIG. 6.

An increased rate in glucose clearance was also observed in the non-diabetic group after the first and second MPC treatments (FIG. 7 Panel a). The increase is shown as the mean percent change in glucose clearance (5-10% for months 1-3 vs 15-25% for months 4-6) in FIG. 7 (Panel b).

In the Diabetic group both the first and second MPC doses sequentially demonstrated a steady increased rate of glucose clearance that sustained for 6 months at 10-20% relative to baseline as shown in FIG. 7 (Panel b). These data imply that successive MPC treatments induce progressive increase in the glucose clearance rate after iv glucose loading.

Administration of MPCs was also shown to induce a sustained reduction in mean monthly blood glucose levels and improve fasting insulin levels (FIG. 8). In the non-diabetic animal #1880 (mean baseline of 80 mg/dL) the first dose of MPC produced a reduction in the fasting glucose level. Animal #1880 also showed a reduction in fasting insulin level after the first dose.

Animal #3351 showed a reduction in fasting BGL after the 2nd month of the second MPC dose. This animal (which was hyperinsulinemic at baseline prior to MPC therapy) showed normalization of insulin levels for 6 months after MPC infusion.

All diabetic animals demonstrated a profound reduction in fasting BGL after MPC treatment values (sustained below baseline for 6 months) compared to pretreatment baseline. These data demonstrate that MPC treatment induces a sustained reduction in mean monthly blood glucose levels.

FIG. 9 shows that in the non-diabetic group both the first and second MPC doses produced a reduction in the fasting glucose level compared to baseline values prior to MPC treatment. After MPC infusion there was also a sustained normalization of insulin levels for 6 months. In the diabetic group there was a profound reduction in fasting BGL after MPC treatment compared to pretreatment baseline values and was sustained for 6 months below baseline. Furthermore, in the diabetic group the first MPC reduced the fasting insulin levels compared to pretreatment baseline values. These data demonstrate that MPC treatment induces a sustained reduction in mean monthly fasting blood glucose levels. There was a sustained reduction in fasting insulin levels in non-diabetic animals suffering from metabolic syndrome for 6 months, and this effect was transient for 3 months in the diabetic group.

FIG. 9(a) shows the mean monthly body weight changes in both Non-Diabetic and Diabetic animals Individual data for the Non-Diabetic and Diabetic animals for a month before and 6 months after MPC treatment are demonstrated. Arrows indicate the time at which MPCs were infused. Dosage of MPC for each animal is shown on the top of each panel.

As shown in FIG. 10 Panel (a), the first MPC dose had a transient effect on weight loss and the second dose of MPC had a progressive effect on weight loss in non-diabetic animal #1880 compared to pretreatment body weights. Non-diabetic animal #3351 showed a progressive weight loss pattern with both doses of MPC. The weight loss surprisingly occurred despite stable food consumption throughout the period of weight measurements as shown in FIG. 10 Panel (b) for each individual animal.

In diabetic animals #1624 and #7581, there was a consistent body weight loss after the first and second dose of MPC. Body weight of animal #2875 was below untreated baseline throughout MPC treatment.

FIG. 10 Panel (c) shows the mean monthly percentage weight loss in the pooled group of animals after MPC therapy relative to the untreated baseline. The weight loss ranged from 4% to 6% during the course of MPC treatment. These data demonstrate that MPC treatment induce weight loss in both Non-Diabetic and Diabetic animals that is associated with reduced fasting blood glucose levels, increased glucose clearance rates and induced glucose stimulated insulin production after MPC treatment.

FIG. 11 shows that in non-diabetic animals, there was a sustained reduction in triglyceride and VLDL and increments in HDL levels after MPC therapy compared to the pretreatment values. In animal #1880, there was also evidence of an effect of the second dose of MPCs, which showed an increase in the lipoprotein index after the second MPC dose compared to the first MPC dose. Both non-diabetic animals demonstrated a sustained increase in the lipoprotein index for 6 months. The data presented in FIG. 11 demonstrate that MPC treatment improves lipid profiles long term in non-diabetic animals and short-term in diabetic animals.

In the non-diabetic group there was a sustained reduction in triglyceride and VLDL and increments in HDL levels after MPC therapy compared to the pretreatment values for a duration of 6 months (FIG. 12). In concordance with the lipid profile changes, the non-diabetic group demonstrated a sustained increase in lipoprotein index for 6 months. Diabetic animals showed short-term effects following the first dose of MPC on the lipoprotein index that lasted for a period of 2 months. These data demonstrate that MPC treatment improves lipid profiles long term in non-diabetic animals and short-term in diabetic animals.

The data presented herein demonstrate that the Mauritian cynomolgous monkeys studied have diet induced metabolic syndrome and that progression to type 2 diabetes is associated with reduced insulin levels and a defect in late-phase insulin responses to glucose loading. Successive MPC doses 3 months apart result in progressive augmentation of late-phase insulin responses to glucose loading and improvement in glucose clearance over 6 months. Furthermore, intravenous MPC infusion normalizes fasting blood glucose levels over 6 months, without any hypoglycaemia. MPC treatment also results in progressive weight loss over 6 months and normalizes the aberrant lipid profile associated with metabolic syndrome. Lipid lowering effects are sustained over 6 months in subjects without diabetes.

The invention claimed is:

1. A method for treating excessive weight or obesity or for treating metabolic syndrome or a symptom thereof, comprising administering an effective amount of a population of cells enriched for STRO-1$^+$ cells and/or progeny thereof and/or soluble factors derived therefrom to a subject suffering from excessive weight or obesity or metabolic syndrome or a symptom thereof.

2. The method of claim 1, comprising administering an amount of the population enriched for STRO-1$^+$ cells and/or the progeny and/or the soluble factors sufficient to reduce body weight by at least about 3% about 4 weeks after the administration.

3. The method of claim 1, wherein the symptom of metabolic syndrome is selected from the group consisting of elevated triglycerides, elevated low density lipoproteins, reduced high density lipoproteins, reduced lipoprotein index, elevated fasting glucose levels, elevated fasting insulin, reduced glucose clearance following feeding, insulin resistance, impaired glucose tolerance, obesity and combinations thereof.

4. The method of claim 1, comprising administering an amount of the population enriched for STRO-1$^+$ cells and/or the progeny and/or the soluble factors sufficient to result in one or more of the following:
   (i) reduce triglycerides;
   (ii) reduce low density lipoproteins;
   (iii) increase high density lipoproteins;
   (iv) increase lipoprotein index;
   (v) reduce fasting glucose levels;
   (vi) increase insulin secretion by the pancreas;
   (vii) increase glucose clearance following feeding;
   (viii) reduce insulin resistance; and
   (ix) reduce body weight.

5. The method of claim 1 comprising administering a population of cells enriched for STRO-1$^{bright}$ cells and/or progeny thereof and/or soluble factors derived therefrom.

6. The method of claim 1, wherein the population enriched for STRO-1$^+$ cells and/or progeny thereof and/or soluble factors derived therefrom are administered systemically.

7. The method of claim 6, wherein the population and/or the progeny and/or the soluble factors are administered a plurality of times.

8. The method of claim 7, wherein the population and/or the progeny and/or the soluble factors are administered once every four or more weeks.

9. The method of claim 1 comprising administering a dose of the population enriched for STRO-1$^+$ cells and/or the progeny and/or the soluble factors sufficient to achieve one or more of the following:
   (i) reduce triglycerides;
   (ii) reduce low density lipoproteins;
   (iii) increase high density lipoproteins;
   (iv) increase lipoprotein index;
   (v) reduce fasting glucose levels;
   (vi) increase insulin secretion by the pancreas;
   (vii) increase glucose clearance following feeding;
   (viii) reduce insulin resistance; and
   (ix) reduce body weight.

10. The method of claim 1, comprising administering between $0.1 \times 10^6$ to $5 \times 10^6$ STRO-1$^+$ cells and/or progeny thereof per kg.

11. The method of claim 10, comprising administering between $0.3 \times 10^6$ to $2 \times 10^6$ STRO-1$^+$ cells and/or progeny thereof per kg.

12. The method of claim 1 comprising administering a low dose of STRO-1$^+$ cells and/or progeny thereof.

13. The method of claim 12, wherein the low dose of STRO-1$^+$ cells and/or progeny thereof comprises between $0.1 \times 10^5$ and $0.5 \times 10^6$ STRO-1$^+$ cells and/or progeny thereof per kg.

14. The method of claim 12, wherein the low dose of STRO-1$^+$ cells and/or progeny thereof comprises about $0.3 \times 10^6$ STRO-1$^+$ cells and/or progeny thereof per kg.

15. The method of claim 1, wherein the population enriched for STRO-1$^+$ cells and/or progeny cells are autogeneic or allogeneic and/or the soluble factors can be derived from autogeneic or allogeneic cells.

16. The method of claim 1, wherein the population enriched for STRO-1$^+$ cells and/or progeny cells have been culture expanded prior to administration and/or prior to obtaining the soluble factors.

17. The method of claim 1, wherein the population enriched for STRO-1$^+$ cells are STRO-1$^{bri}$, and/or express tissue non-specific alkaline phosphatase (TNAP) and/or the progeny cells and/or soluble factors are derived from STRO-1$^+$ cells that are STRO-1$^{bri}$ and/or express TNAP.

18. The method of claim 1, wherein the STRO-1$^+$ cells and/or progeny cells thereof and/or soluble factors derived therefrom are administered in the form of a composition comprising said STRO-1$^+$ cells and/or progeny cells thereof and/or soluble factors derived therefrom and a carrier and/or excipient.

* * * * *